US006487445B1

(12) United States Patent
Serita et al.

(10) Patent No.: US 6,487,445 B1
(45) Date of Patent: Nov. 26, 2002

(54) METHOD AND APPARATUS FOR MEASURING DISTRIBUTION OF BODY FAT

(75) Inventors: Eiichi Serita, Tokyo (JP); Hiroki Hasegawa, Tokyo (JP); Hideki Hosoi, Ohmagari (JP)

(73) Assignee: Tanita Corporation, Tokyo (JP)

( * ) Notice: Subject to any disclaimer, the term of this patent is extended or adjusted under 35 U.S.C. 154(b) by 116 days.

(21) Appl. No.: 09/590,675

(22) Filed: Jun. 9, 2000

(30) Foreign Application Priority Data

Jun. 11, 1999 (JP) .......................................... 11-164633
Jun. 11, 1999 (JP) .......................................... 11-164634

(51) Int. Cl.[7] ................................................ A61B 5/00
(52) U.S. Cl. ...................................... 600/547; 600/587
(58) Field of Search ............................ 600/547, 587, 600/595

(56) References Cited

U.S. PATENT DOCUMENTS

| | | | | |
|---|---|---|---|---|
| 4,949,727 A | * | 8/1990 | Yamazaki et al. | 128/734 |
| 5,435,315 A | * | 7/1995 | McPhee et al. | 128/670 |
| 5,579,782 A | * | 12/1996 | Masuo | 128/734 |
| 5,611,351 A | | 3/1997 | Sato et al. | 128/734 |

FOREIGN PATENT DOCUMENTS

| | | |
|---|---|---|
| EP | 0545014 A1 | 6/1993 |
| GB | 2176323 A | 12/1986 |

OTHER PUBLICATIONS

European Search Report dated Nov. 15, 2000.

* cited by examiner

*Primary Examiner*—Max Hindenburg
(74) *Attorney, Agent, or Firm*—McDermott, Will & Emery

(57) ABSTRACT

The present invention relates to a method and an apparatus for measuring a distribution of body fat for human body. The method comprises the step of measuring a bioelectrical impedance and a thickness of abdominal subcutaneous fat, based on the personal data such as sex, age, height, weight, etc. The method further comprises the step of calculating an area or an amount of abdominal visceral fat or abdominal subcutaneous fat, based on the measurements of the bioelectrical impedance and the thickness of abdominal subcutaneous fat as well as the girth of abdomen. According to another embodiment of the present invention, the method comprises the step of measuring the thickness of abdominal subcutaneous fat and the girth of abdomen. Thereafter, the area of abdominal visceral fat and the area of abdominal subcutaneous fat are calculated, based upon the measurements of the thickness of abdominal subcutaneous fat and the girth of abdomen.

55 Claims, 18 Drawing Sheets

CORRELATION BETWEEN TOTAL AMOUNT OF FAT
AND TOTAL AREA OF FAT IN ABDOMEN

TOTAL AMOUNT OF FAT
r=0.90, p<0.005

CORRELATION BETWEEN THICKNESS AND
AREA OF ABDOMINAL SUBCUTANEOUS FAT

THICKNESS OF ABDOMINAL
SUBCUTANEOUS FAT
r=0.84, p<0.005

CORRELATION BETWEEN TOTAL AMOUNT OF FAT AND AREA OF ABDOMINAL VISCERAL FAT

TOTAL AMOUNT OF FAT
$r=0.79$, $p<0.005$

CORRELATION BETWEEN THICKNESS OF ABDOMINAL SUBCUTANEOUS FAT AND TOTAL AMOUNT OF SUBCUTANEOUS FAT

THICKNESS OF ABDOMINAL
SUBCUTANEOUS FAT
$r=0.78$, $p<0.005$

CORRELATION BETWEEN TOTAL SUBCUTANEOUS FAT
AND AREA OF ABDOMINAL SUBCUTANEOUS FAT

TOTAL SUBCUTANEOUS FAT
$r=0.80$, $p<0.005$

CORRELATION BETWEEN AMOUNT OF VISCERAL FAT
AND AREA OF ABDOMINAL VISCERAL FAT

AMOUNT OF VISCERAL FAT
$r=0.83$, $p<0.005$

CORRELATION BETWEEN HEIGHT, WEIGHT AND THICKNESS OF SUBCUTANEOUS FAT, AND TOTAL AMOUNT OF SUBCUTANEOUS FAT

HEIGHT^0.725*WEIGHT^0.425*THICKNESS OF SUBCUTANEOUS FAT $r=0.90, p<0.005$

CORRELATION BETWEEN PRODUCT OF WAIST SIZE AND THICKNESS OF SUBCUTANEOUS FAT, AND AREA OF ABDOMINAL SUBCUTANEOUS FAT

PRODUCT OF WAIST SIZE AND THICKNESS OF SUBCUTANEOUS FAT $r=0.93, p<0.005$ (STEP 1) START (SWITCH ON)
(STEP 2) ENTER SEX
(STEP 3) ENTER AGE OR DATE OF BIRTH
(STEP 4) ENTER HEIGHT
(STEP 5) MEASURE THICKNESS OF SUBCUTANEOUS FAT
(STEP 6) MEASURE GIRTH
(STEP 7) ARITHMETIC OPERATION
(STEP 8) DISPLAY
(STEP 9) SWITCH OFF

CORRELATION BETWEEN WAIST SIZE AND TOTAL AREA OF FAT IN ABDOMEN

WAIST SIZE
r=0.87, p<0.005

CORRELATION BETWEEN WAIST SIZE AND AREA OF VISCERAL FAT

WAIST SIZE
r=0.67, p<0.005

METHOD AND APPARATUS FOR MEASURING DISTRIBUTION OF BODY FAT

BACKGROUND OF THE INVENTION

1. Field of the Invention

The present invention relates to a method and an apparatus for measuring a body fat for a person, and more particularly, to a method and an apparatus for measuring a distribution of body fat for a human body.

2. Description of the Prior Art

In the past, the weight of a person was frequently used as a factor to represent a personal health condition. But, recently, a rate of body fat for a person has becoming to be an important factor to represents the health condition for the person. Accordingly, various types of method and apparatus for measuring an amount of body fat have been developed and proposed. For instance, TOKUKAISHO No. 62-169023 discloses a technique for measuring an amount of body fat for a person by entering the personal data such as height, age, sex, etc., and measuring the weight for a person and the impedance between the extreme parts on a body of the person. In addition, TOKUHYOSHO No. 57-500900 discloses a technique for measuring the thickness of a fatty fascia. According to this technique, an ultrasonic pulse signal is applied to an animal from the rear side, and any received signal reflected from a boundary between a fatty fascia and a muscle fascia is detected. Then the time period between transmission and reception of the pulse signal is measured to determine the thickness of the fatty fascia. Furthermore, TOKUKAISHO No. 62-87139 discloses an estimating method for body fat. According to this method, subcutaneous fat on each part of a human body is measured by using an ultrasonic signal. Then the measurement is multiplied by a cross sectional area factor or a body fat estimation factor on each part of the body for producing an estimate of body fat on each part of the body. Thereafter, the individual estimates are integrated to determine whole body fat.

Recently, it has found that a risk for a person to get so called "adult (noncommunicable) diseases", such as diabetes, arteriosclerosis, etc., may vary depending upon the distribution of fat or whether he has a subcutaneous fat or a visceral fat, irrespective of the same rate of fat he has. Therefore, a method of measuring the distribution of fat by analyzing a tomographic image of an abdomen taken by CT or MRI has been proposed.

Such method, however, is problematic in that the analysis of the image is highly complex and CT may produce an exposure of X-ray to the human body.

Therefore, an object of the present invention is to provide a method and an apparatus for measuring a distribution of body fat, that can solve the problems of the prior art.

SUMMARY OF THE INVENTION

In order to attain such object, the prior art problems are solved, according to one aspect of the present invention, by providing a new and improved method of measuring a distribution of body fat for a human body, characterized in that it comprises the steps of: measuring a bioelectrical impedance and a thickness of abdominal subcutaneous fat, based on the personal data such as sex, age, height, weight, etc.; and calculating an area or an amount of abdominal visceral fat, based on the measurements of the bioelectrical impedance and the thickness of abdominal subcutaneous fat.

According to another aspect, the present invention provides a method of measuring a distribution of body fat for a human body, characterized in that it comprises the steps of: measuring a bioelectrical impedance and a thickness of abdominal subcutaneous fat, based on the personal data such as sex, age, height, weight, etc.; and calculating an area or an amount of abdominal subcutaneous fat, based on the measurements of the bioelectrical impedance and the thickness of abdominal subcutaneous fat.

According to further aspect, the present invention provides a method of measuring a distribution of body fat for a human body, characterized in that it comprises the steps of: measuring a bioelectrical impedance and a thickness of abdominal subcutaneous fat, based on the personal data such as sex, age, height, weight, etc.; and calculating an area or an amount of abdominal visceral fat and an area or an amount of abdominal subcutaneous fat, based on the measurements of the bioelectrical impedance and the thickness of abdominal subcutaneous fat.

According to yet further aspect, the present invention provides a method of measuring a distribution of body fat for a human body, characterized in that it comprises the steps of: measuring a bioelectrical impedance and a thickness of abdominal subcutaneous fat, based on the sex, age, height and weight of a person; measuring a girth of abdomen; and calculating an area or an amount of abdominal visceral fat, based on the measurements of the bioelectrical impedance, the thickness of abdominal subcutaneous fat and the girth of abdomen.

According to one embodiment of the present invention, said thickness of abdominal subcutaneous fat is measured by using an ultrasonic signal.

According to one embodiment of the present invention, said thickness of abdominal subcutaneous fat is measured by using a skin hold caliper.

According to yet further aspect, the present invention provides an apparatus for measuring a distribution of body fat for a human body, characterized in that it comprises: a first input unit that enters the personal data such as sex, age, height, weight, etc.; a measuring unit that measures a bioelectrical impedance; a second input unit that enters a thickness of abdominal subcutaneous fat; and an arithmetic element that calculates an area or an amount of abdominal visceral fat, based on the data from said first input unit, said measuring unit and said second input unit.

According to yet further aspect, the present invention provides an apparatus for measuring a distribution of body fat for a human body, characterized in that it comprises: a first input unit that enters the personal data such as sex, age, height, weight, etc.; a measuring unit that measures a bioelectrical impedance; a second input unit that enters a thickness of abdominal subcutaneous fat; and an arithmetic element that calculates an area or an amount of abdominal subcutaneous fat, based on the data from said first input unit, said measuring unit and said second input unit.

According to yet further aspect, the present invention provides an apparatus for measuring a distribution of body fat for a human body, characterized in that it comprises: a first input unit that enters the personal data such as sex, age, height, weight, etc.; a measuring unit that measures a bioelectrical impedance; a second input unit that enters a thickness of abdominal subcutaneous fat; a third input unit that enters a girth of abdomen; and an arithmetic element that calculates an area or an amount of abdominal visceral fat, based on the data from said first input unit, said measuring unit, said second input unit and said third input unit.

According to yet further aspect, the present invention provides an apparatus for measuring a distribution of body fat for human body, characterized in that it comprises: a first input unit that enters the personal data such as sex, age, height, weight, etc.; a measuring unit that measures a bioelectrical impedance; a second input unit that enters a thickness of abdominal subcutaneous fat; a third input unit that enters a girth of abdomen; and an arithmetic element that calculates an area or an amount of abdominal subcutaneous fat, based on the data from said first input unit, said measuring unit, said second input unit and said third input unit.

According to yet further aspect, the present invention provides an apparatus for measuring a distribution of body fat for human body, characterized in that it comprises: a first input unit that enters the personal data such as sex, age, height, weight, etc.; a measuring unit that measures a bioelectrical impedance; a second input unit that enters a thickness of abdominal subcutaneous fat; and an arithmetic element that calculates an area or an amount of abdominal visceral fat and an area or an amount of abdominal subcutaneous fat, based on the data from said first input unit, said measuring unit and said second input unit.

According to one embodiment of the present invention, said second input unit includes an ultrasonic probe.

According to another embodiment of the present invention, the data detected by said ultrasonic probe is transmitted to said arithmetic element via a radio communication means or an optical communication means According to further embodiment of the present invention, said second input unit includes a skin hold caliper.

According to further embodiment of the present invention, the data detected by said skin hold caliper is transmitted to said arithmetic element via a radio communication means or an optical communication means According to yet further aspect, the present invention provides an apparatus for measuring a distribution of body fat for a human body, characterized in that it comprises: a first arithmetic element that calculates an area of abdominal visceral fat; a second arithmetic element that calculates an area of abdominal subcutaneous fat; and a decision unit that determines the type of corpulence by dividing the area of abdominal visceral fat calculated in said first arithmetic element by the area of abdominal subcutaneous fat calculated in said second arithmetic element.

According to yet further aspect, the present invention provides a method of measuring a distribution of body fat for a human body, characterized in that it comprises the steps of: measuring the thickness of abdominal subcutaneous fat and the girth of abdomen; and calculating the area of abdominal visceral fat, based upon the measurements of the thickness of abdominal subcutaneous fat and the girth of abdomen.

According to yet further aspect, the present invention provides a method of measuring a distribution of body fat for a human body, characterized in that it comprises the steps of: measuring the thickness of abdominal subcutaneous fat and the girth of abdomen; and calculating the area of abdominal subcutaneous fat, based upon the measurements of the thickness of abdominal subcutaneous fat and the girth of abdomen.

According to yet further aspect, the present invention provides a method of measuring a distribution of body fat for a human body, characterized in that it comprises the steps of: measuring the thickness of abdominal subcutaneous fat and the girth of abdomen; and calculating the area of abdominal visceral fat and the area of abdominal subcutaneous fat, based upon the measurements of the thickness of abdominal subcutaneous fat and the girth of abdomen.

According to one embodiment of the present invention, the step of deriving the area of abdominal visceral fat or the area of abdominal subcutaneous fat further comprises the step of performing a correction process based upon the personal data including sex, age, height, etc.

According to yet further aspect, the present invention provides an apparatus for measuring a distribution of body fat for a human body, characterized in that it comprises: a first input unit that enters the thickness of abdominal subcutaneous fat; a second input unit that enters the girth of abdomen; and an arithmetic element that calculates the area of abdominal visceral fat based upon the data from said first and second input units.

According to one embodiment of the present invention, said first input unit includes an ultrasonic probe.

According to another embodiment of the present invention, said first input unit includes a skin hold caliper.

According to further embodiment of the present invention, the apparatus further comprises a third input unit that enters the personal data including sex, age, height, etc.

BRIEF DESCRIPTION OF THE DRAWINGS

Now the preferred embodiments of the present invention will be described with reference to the accompanying drawings.

DESCRIPTION OF THE PREFERRED EMBODIMENTS

Figure 1:
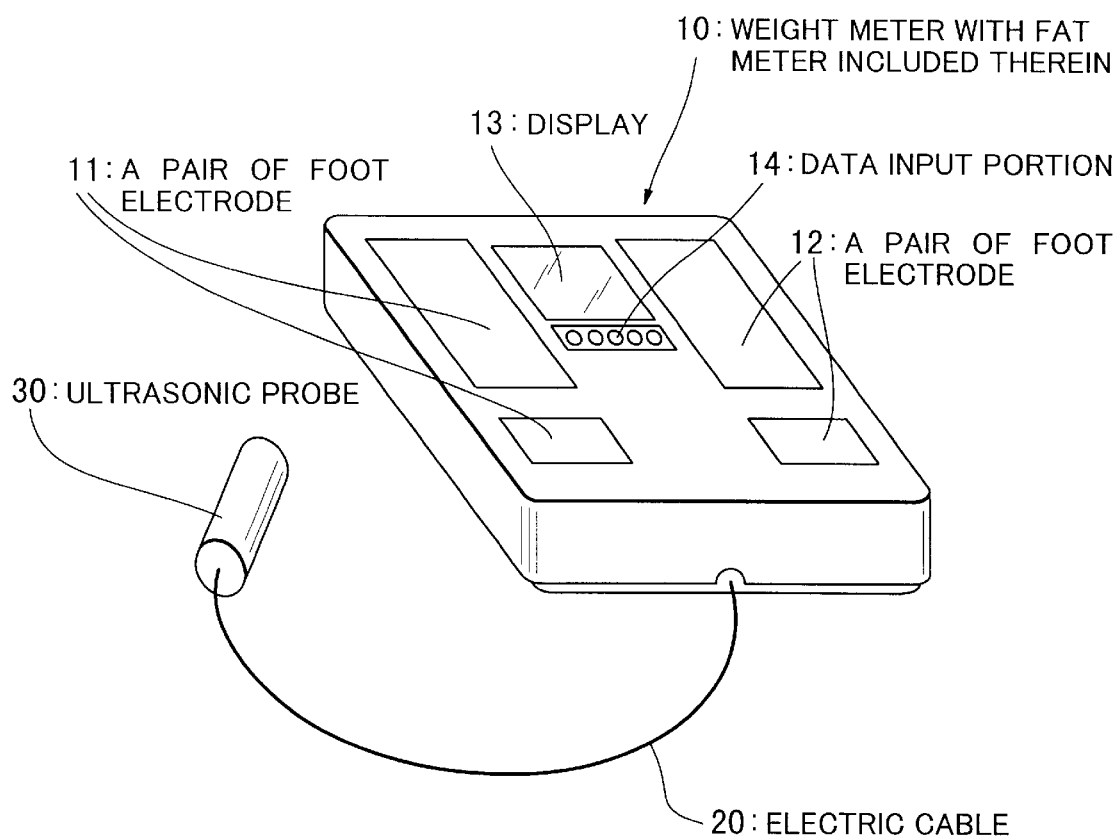
FIG. 1 is a perspective view representing an apparatus for measuring a body fat for a person according to a preferred embodiment of the present invention.

FIG. 1 is a perspective view representing an apparatus for measuring a body fat for a person according to a preferred embodiment of the present invention. The body fat measuring apparatus includes a weight meter 10 with a fat meter included therein, and an ultrasonic probe 30 connected to the weight meter 10 via an electric cable 20. In this embodiment, some standard electric cable 20 is shown to connect the ultrasonic probe 30 with the weight meter 10. But it may possible that the measurement data obtained by the ultrasonic probe 30 is transmitted to the weight meter 10 via a radio frequency communication or an optical communication.

The weight meter 10 is provided with a power switch (not shown), pairs of foot electrodes 11 and 12, a display 13 and a data input portion 14 on the top of the meter housing. In addition, a weight sensor and a control circuit having an arithmetic component are included inside the housing of weight meter 10.

Figure 2:
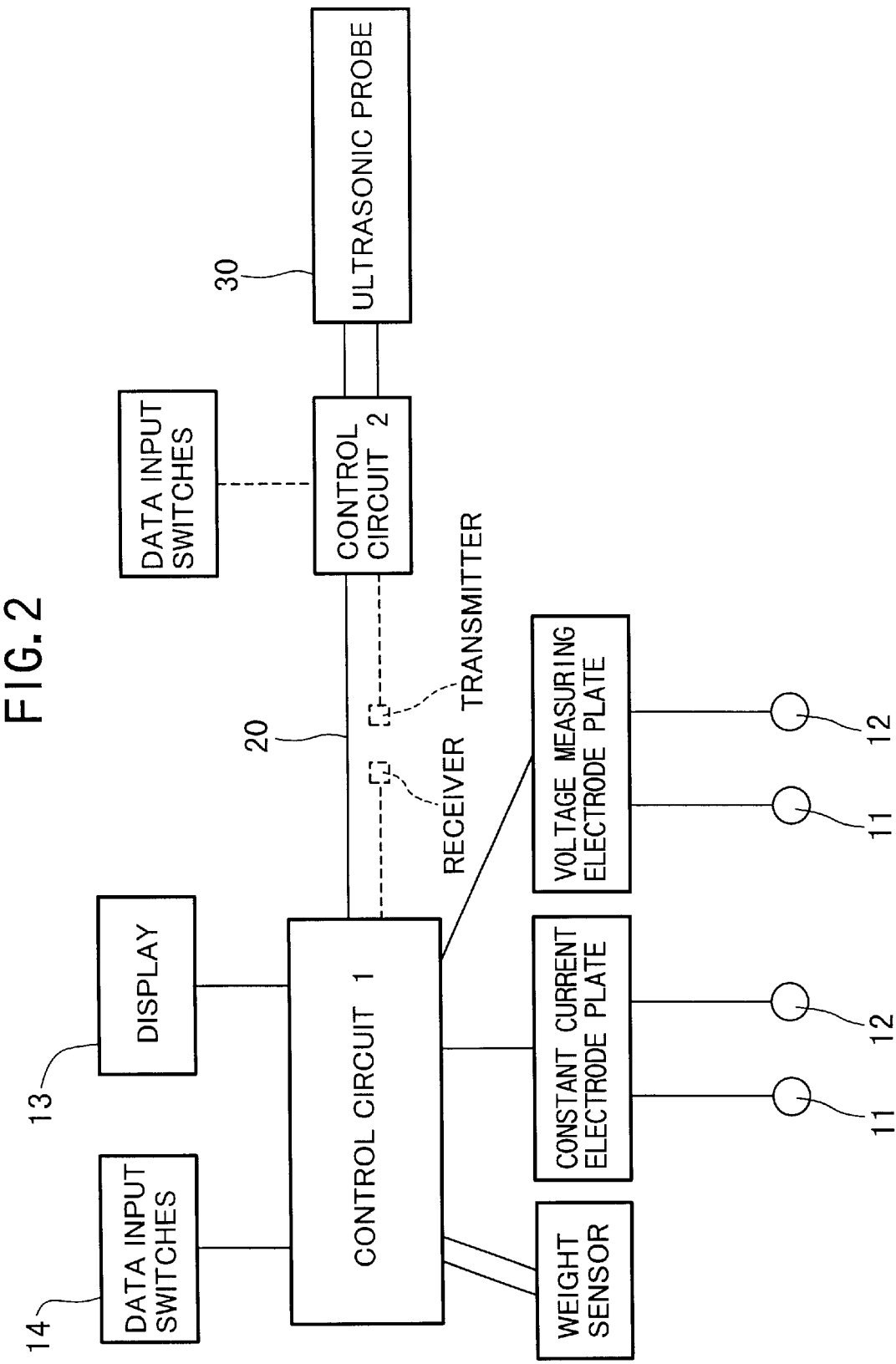
FIG. 2 is a schematic block diagram representing the circuit configuration of the body fat measuring apparatus, as shown in FIG. 1.

FIG. 2 is a schematic block diagram representing a circuit configuration of the body fat measuring apparatus, as shown in FIG. 1. As shown in FIG. 2, the weight meter 10 includes a control circuit 1 as the main component within the housing, as usual. The control circuit 1 functions to receive a data from data input switches on the data input portion 14, and a weight data detected by the weight sensor. In addition, it receives data signals from constant current electrode plates and voltage measuring electrode plates of the pairs of foot electrodes 11 and 12, and a data from the ultrasonic probe 30. Based on those data, the control circuit performs arithmetic operations, as described below, for indicating the results of the arithmetic operations on the display 13.

Alternative to the control circuit 1 and the data input switches 14 positioned on the weight meter 10, the similar control circuit 2 and the data input switches may be positioned on the ultrasonic probe 30, as shown in FIG. 2. In addition, instead of the electric cable 20, the radio frequency communication or optical communication may be done for data transmission between transmitter/receiver portions in the weight meter 10 and the ultrasonic probe 30, as indicated by a broken line in FIG. 2.

Figure 3:
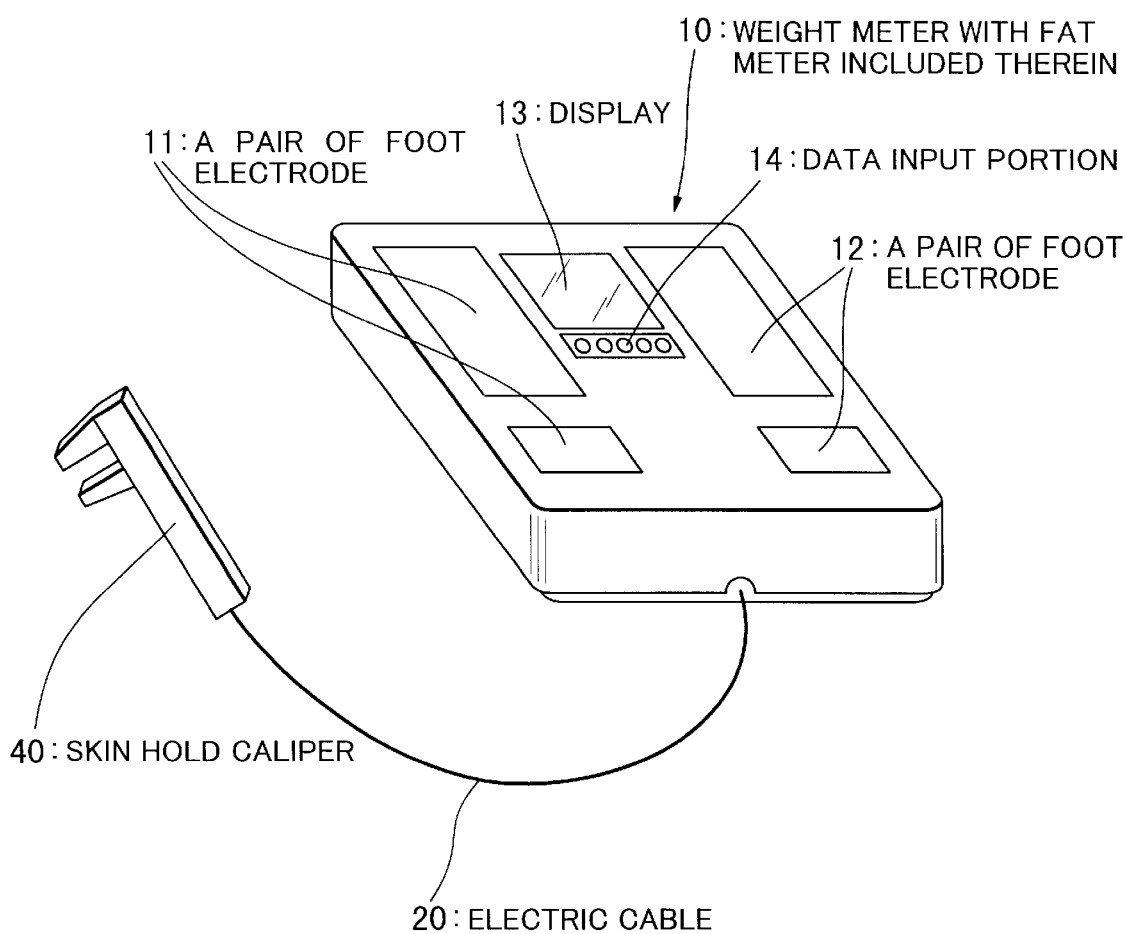
FIG. 3 is a perspective view representing an apparatus for measuring a body fat for a person according to another embodiment of the present invention.

FIG. 3 is a perspective view representing an apparatus for measuring a body fat for a person according to another embodiment of the present invention. The body fat measuring apparatus includes a weight meter 10 with a fat meter included therein, and a skin hold caliper 40 connected to the weight meter 10 via an electric cable 20. In this embodiment, some standard electric cable 20 is shown to connect the skin hold caliper 40 with the weight meter 10. But, as already described earlier, it may possible that the measurement data obtained by the skin hold caliper 40 is transmitted to the weight meter 10 via a radio frequency communication or an optical communication.

Similar to the embodiment as above, the weight meter 10 is provided with a power switch (not shown), pairs of foot electrodes 11 and 12, a display 13 and a data input portion 14 on the top of the meter housing. In addition, a weight sensor and a control circuit having an arithmetic component are included inside the housing of weight meter 10.

Figure 4:
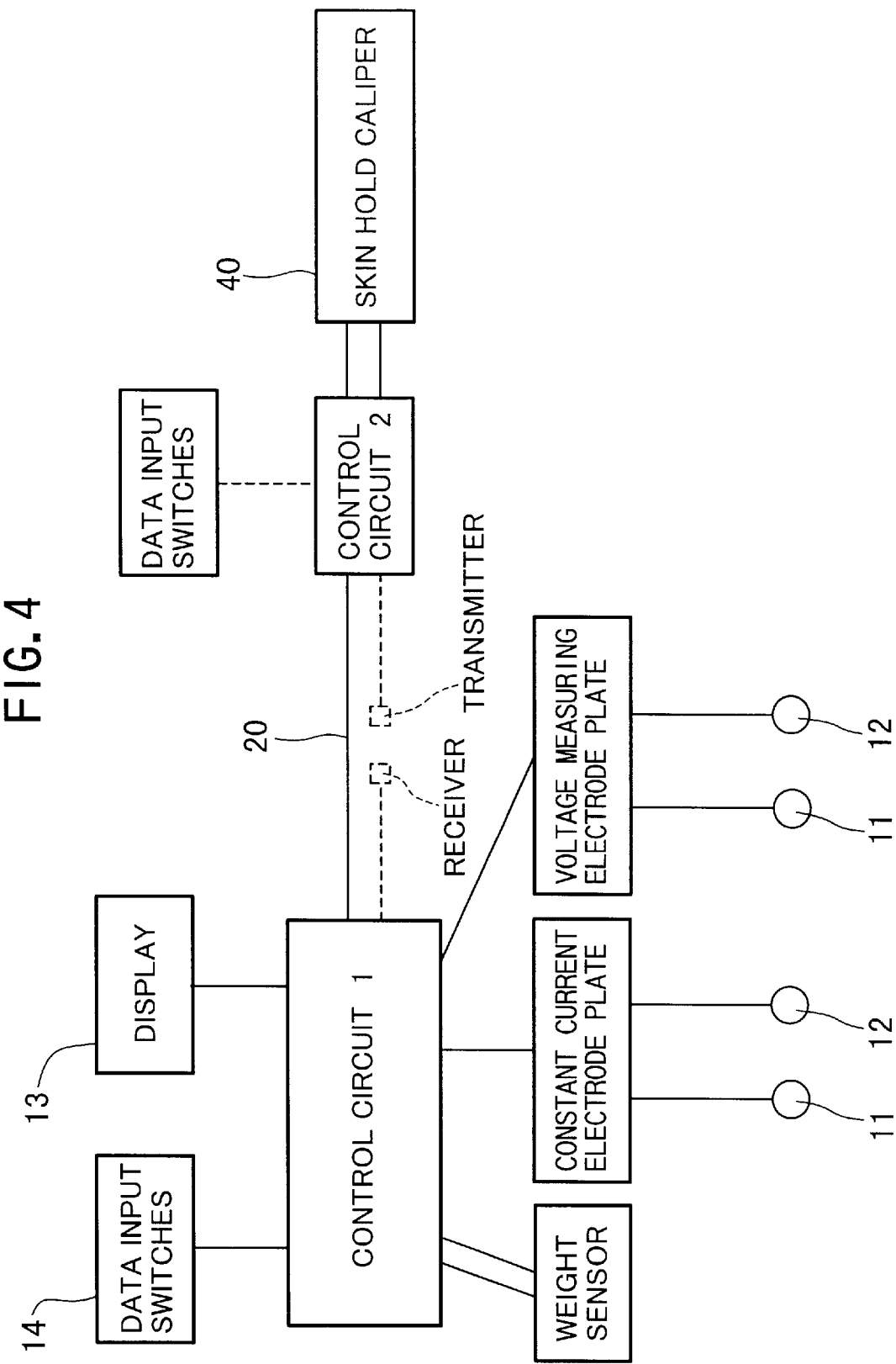
FIG. 4 is a schematic block diagram representing the circuit configuration of the body fat measuring apparatus, as shown in FIG. 3.

FIG. 4 is a schematic block diagram representing a circuit configuration of the body fat measuring apparatus, as shown in FIG. 3. As shown in FIG. 4, the weight meter 10 includes a control circuit 1 as the main component within the housing, as usual. The control circuit 1 functions to receive a data from data input switches on the data input portion 14, and a weight data detected by the weight sensor. In addition, it receives data signals from constant current electrode plates and voltage measuring electrode plates of the pairs of foot electrodes 11 and 12, and a data from the skin hold caliper 40. Based on those data, the control circuit performs arithmetic operations, as described below, for indicating the results of the arithmetic operations on the display 13.

Similar to the embodiment as above, instead of the control circuit 1 and the data input switches 14 positioned on the weight meter 10, the similar control circuit 2 and the data input switches may be positioned on the skin hold caliper 40, as shown in FIG. 4. In addition, instead of the electric cable 20, the radio frequency communication or optical communication may be done for data transmission between transmitter/receiver portions in the weight meter 10 and the skin hold caliper 40, as indicated by a broken line in FIG. 4.

In both embodiments as described above, the weight meter 10 with the fat meter included therein is designed to perform measurement of the bioelectrical impedance between both feet of a person. The present invention is not necessarily be limited to such design, but it may be applied to such configuration that measurement is performed between both hands, between a hand and a foot, between both feet and a hand, as well as between both hands and both feet. The ultrasonic probe 30 functions to measure the thickness of subcutaneous fat in abdomen of a person. In this connection, the measurement may be performed either in "A-mode" which is simple and described latter in detail, or in "B-mode" which takes relatively higher cost. The body fat measuring apparatus in the embodiments as described above use the ultrasonic probe or the skin hold caliper to measure the thickness of subcutaneous fat in abdomen of a person, but they may use other measuring means for performing the same measurement.

Now, a method for measuring a distribution of body fat for a person according to the present invention will be described, in association with the operation of the body fat measuring apparatus in the embodiments as described above.

Figure 5:
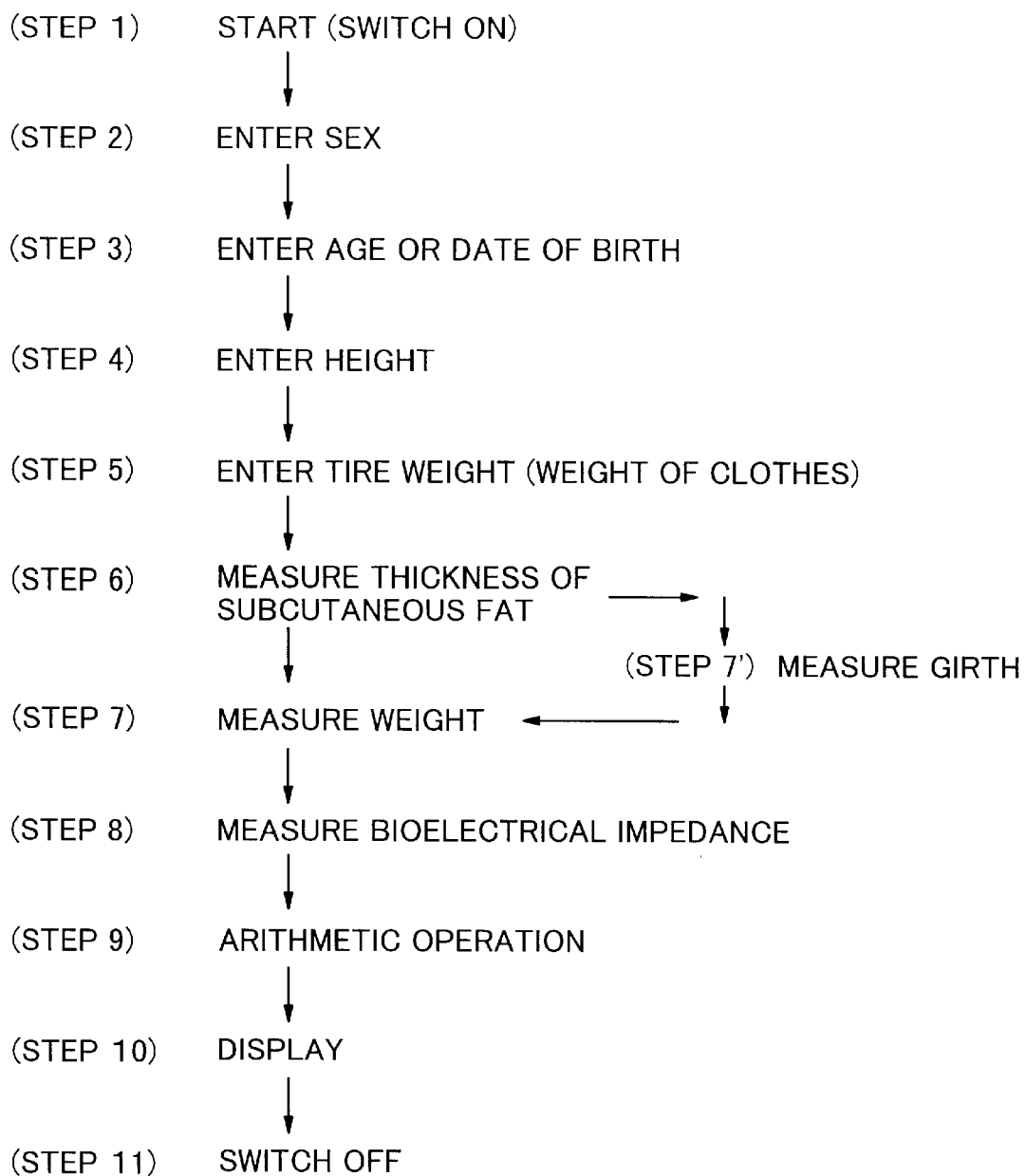
FIG. 5 is a flow chart briefly representing the steps of measuring the distribution of body fat according to the present invention.
Figure 6:
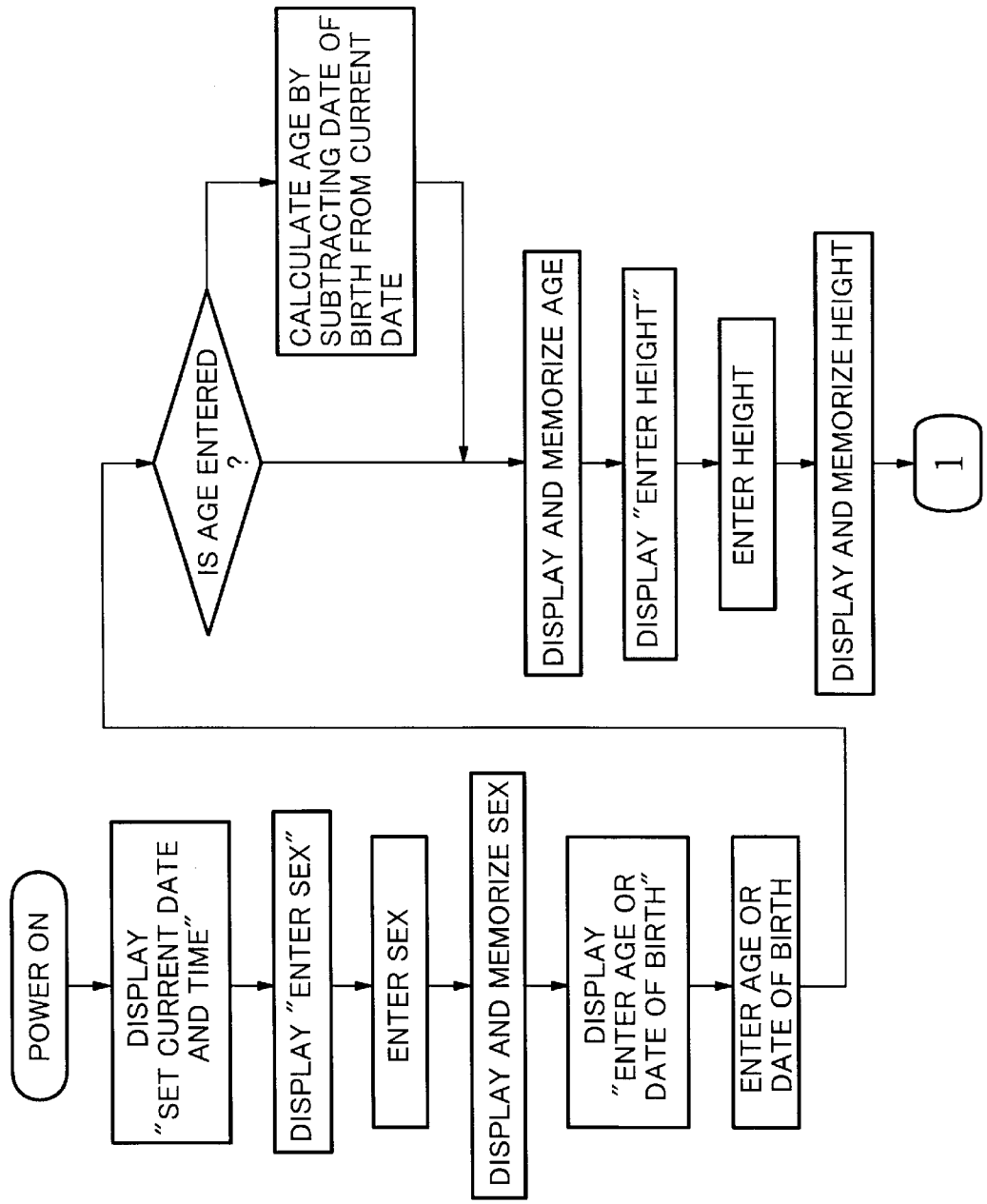
FIGS. 6 and 7 are flow charts each representing in more detail the steps, as shown in FIG. 5.
Figure 7:
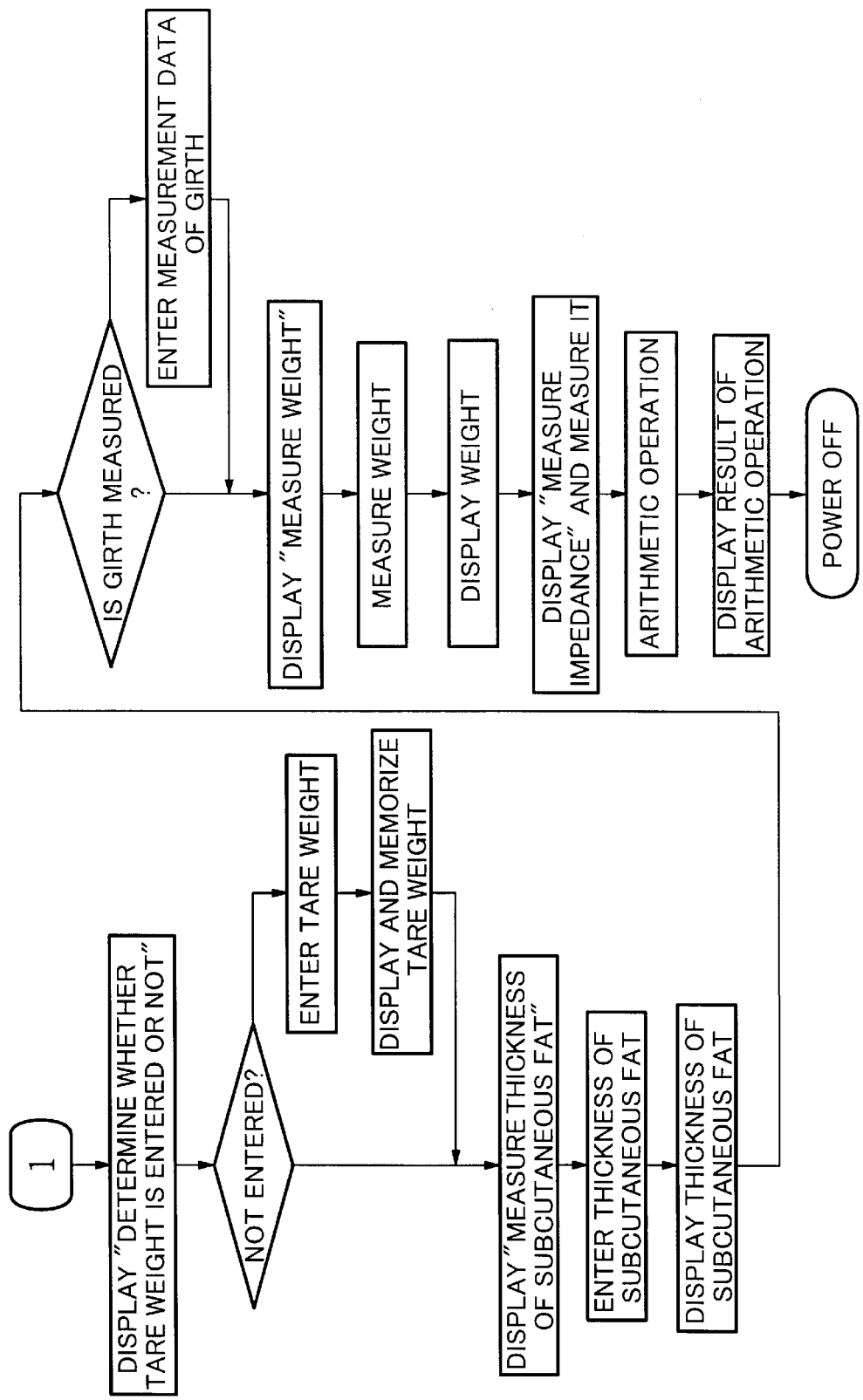

FIG. 5 is a flow chart briefly representing the steps of measuring the distribution of body fat according to the present invention. FIGS. 6 and 7 represent in more detail the steps as shown in FIG. 5 in the form of a flow chart. Referring to FIGS. 5 to 7, a person who wants to measure his distribution of body fat turns on the body fat measuring apparatus, as shown in step 1 in FIG. 5. Then, in steps 2 to 4, he enters the personal data such as his height, age, sex, etc., into the apparatus via the data input switches on the data input portion 14. Then, in step 5, the person enters the weight of the clothes that he wears (or the tare weight). This step 5, however, may be bypassed.

Then, in step 6, the person measures the thickness of subcutaneous fat in his abdomen by using the ultrasonic probe 30 or the skin hold caliper 40. In this connection; the measurement of the thickness of subcutaneous fat in abdomen by the ultrasonic probe 30 is performed in "A-mode" of operation. The measurement data on the thickness of subcutaneous fat in abdomen obtained by the ultrasonic probe 30 or the skin hold caliper 40 is transmitted to the control circuit of the weight meter 10. With regard to "A-mode" of operation for measuring the thickness of subcutaneous fat, the ultrasonic probe 30 produces a high frequency ultrasonic signal that is incident on a surface of the body of the person. Then the ultrasonic signal is reflected from the boundary between a fatty fascia and a peritoneum or between the fatty fascia and a muscle fascia back to the probe 30. Then the time period between the transmission of the ultrasonic signal and the reception of the reflected ultrasonic signal is measured. The thickness of fatty fascia can be determined based upon the time period thus measured and the known velocity value of sound through the fatty fascia.

Then, the person mounts the weight meter 10 with soles of his feet positioned on the pairs of foot electrodes 11 and 12. In step 7, the weight sensor acts to measure the weight of the person, and the weight thus measured is transmitted to the control circuit 1. Then, in step 8, the bioelectrical impedance is measured. In this connection, the bioelectrical impedance is calculated, based upon the detection signals fed to the control circuit 1 from the constant current electrode plates and voltage measuring electrode plates of the foot electrode pairs 11 and 12.

In step 9, the total amount of fat is calculated from the bioelectrical impedance by the arithmetic circuit within the control circuit 1. The calculation of the total amount of fat is performed according to "BIA" process, for instance. In "BIA" process, the impedance between two parts (for instance, between both feet) of a person is measured, and thereafter, the rate of body fat is calculated by utilizing the fact that the relation between a fat tissue and a defatting tissue is closely related to the bioelectrical impedance. Then the rate of body fat is corrected with the personal data such as height, weight, age, etc.

Figure 8:
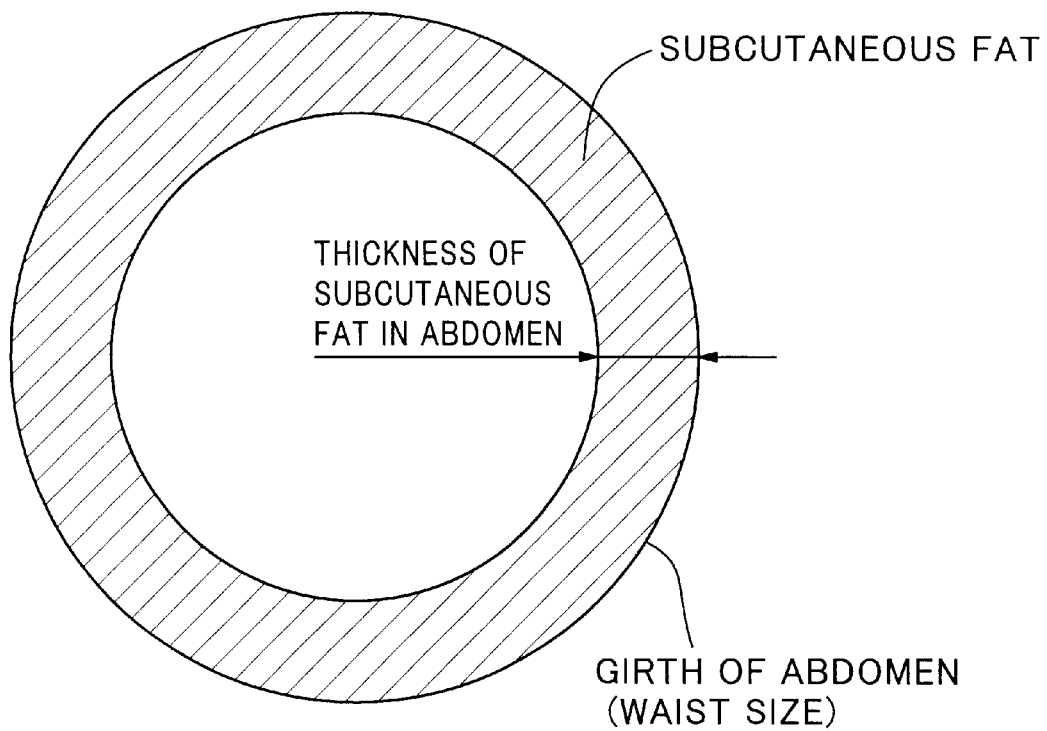
FIG. 8 is a cross sectional view of subcutaneous fat in abdomen when it is assumed that the cross section of abdomen is considered as a true circle.

Based upon the data entered as described above, the arithmetic circuit within the control circuit 1 performs a several operations as follows:

A. (1) Calculation of total area (or cross sectional area) of fat in abdomen:

The total area or amount of fat in abdomen is calculated in relation to the total amount of fat (see FIG. 8).

Figure 9:
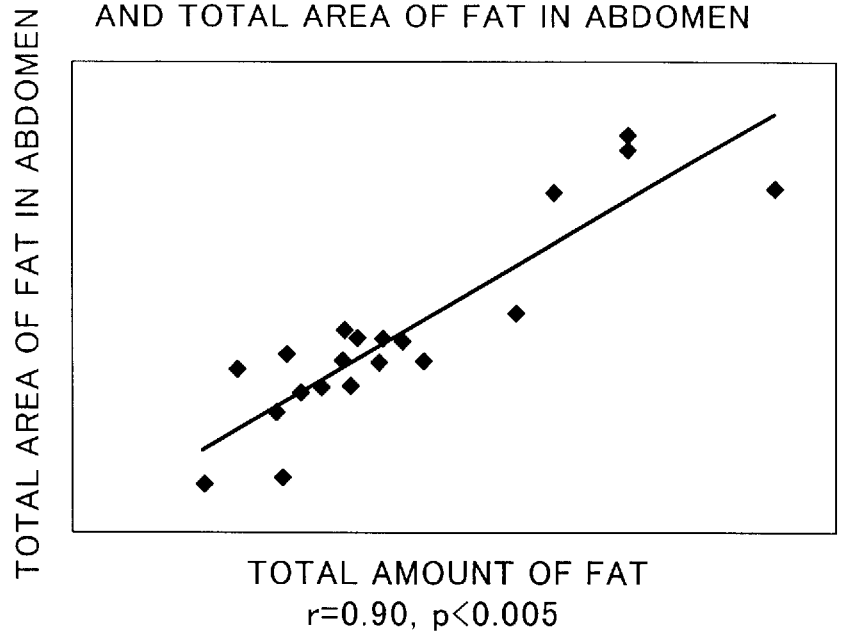
FIG. 9 is a view representing the correlation between a total amount of fat and a total area of fat in abdomen.

At present time, the distribution of fat for a human body is generally consisting of two types: subcutaneous fat and visceral fat (or fat in abdominal cavity). As is well known, the subcutaneous fat is mainly present in abdomen and the visceral fat is also present in the abdomen of a person. Therefore, both types of fats are concentrated in the abdomen of a person. Assuming that the sum of both types of fat is considered as the total amount of fat, the total amount of fat is strongly related to the total area or amount of fat in abdomen. FIG. 9 shows the correlation between the total amount of fat and the total area of fat in abdomen. Due to the correlation present therebetween, a regression curve can be used to determine the total area or amount of fat in abdomen from the total amount of fat.

Before the detailed description with reference to FIGS. 9 to 25, some terms such as Correlation Factor "r", Risk Factor "p<z" and Regression Curve are defined as follows:

As for the correlation factor "r", as this factor "r" approaches "1", any deviation from the regression curve becomes small and the function consisting of both variables "X" and "Y" becomes sensitive. In other words, there is no such possibility present that the change in amount of "Y" becomes unduly greater in relation to the change in amount of "X".

As for the risk factor "p<z", the percentage for which there is no correlation is less than the value of z*100(%).

As for the regression curve, it is represented by the following formula:

$$Y = a \cdot X + b$$

Where "Y" is derived based upon the value "X"; a horizontal axis in the graph represents "X", a vertical axis represents "Y"; and the coefficients "a" and "b" are calculated using the actual measurement values as follows:

$$b = \{\Sigma(X - X[\text{average}]) \cdot (Y - Y[\text{average}])\} / \Sigma\{X - X[\text{average}]\}^2\}$$

$$a = Y[\text{average}] - b \cdot X[\text{average}]$$

Figure 10:
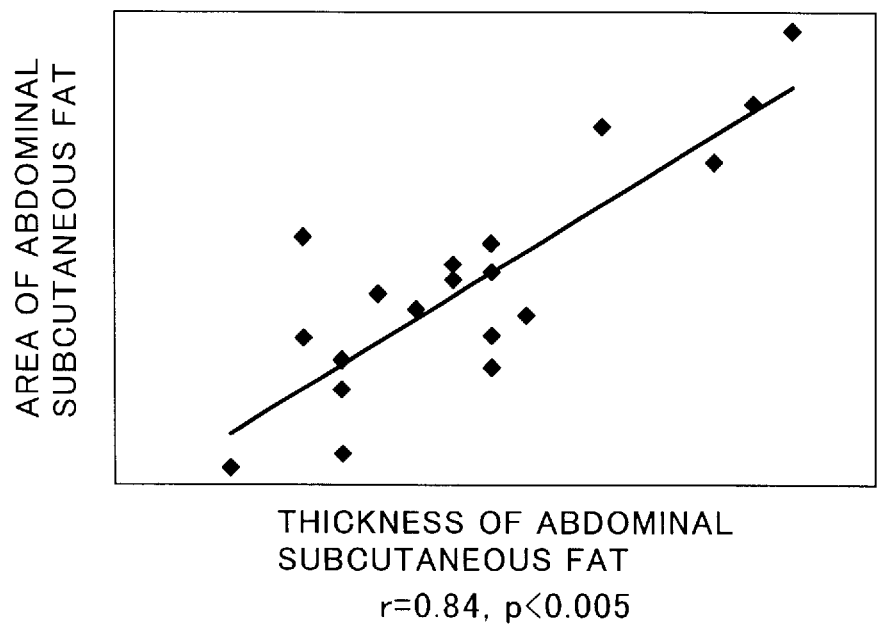
FIG. 10 is a view representing the correlation between a thickness and an area of abdominal subcutaneous fat.
Figure 16:
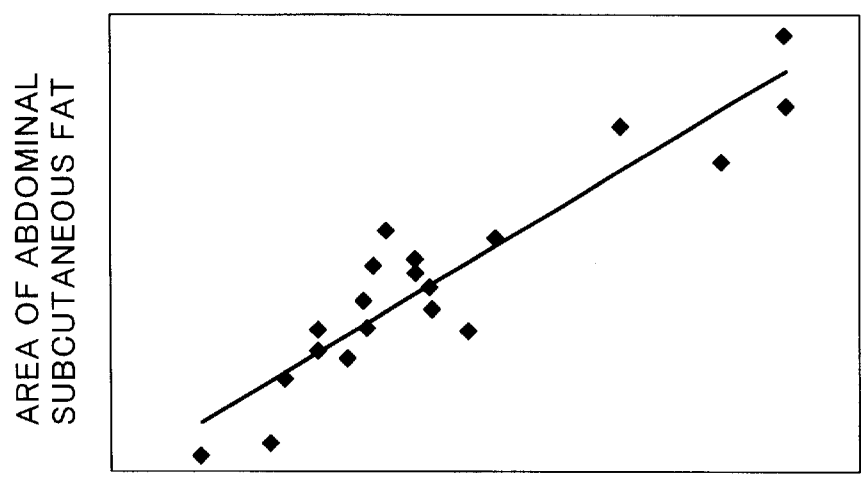
FIG. 16 is a view representing the correlation between a product of waist size and thickness of subcutaneous fat, and an area of abdominal subcutaneous fat.

A. (2) Calculation of an area (or cross sectional area) of subcutaneous fat in abdomen:

The area or amount of subcutaneous fat in abdomen is calculated in relation to the thickness of abdominal subcutaneous fat, or the product of thickness of abdominal subcutaneous fat and waist size (see FIG. 10 or 16). In the latter case, it is required that the girth of waist is measured in step 7' between steps 6 and 7 in FIG. 5.

Referring to FIG. 8, assuming that the abdomen is a true circle in shape, the area (or cross sectional area) of subcutaneous fat in the abdomen is calculated as follows:

Radius of abdomen=waist size/(2π)

Area of subcutaneous fat=(radius of abdomen)$^2 \times \pi$−(radius of abdomen−thickness of abdominal subcutaneous fat)$^2 \times \pi$ Because the thickness of abdominal subcutaneous fat is extremely small, as compared to the girth of abdomen (or waist size), the area of abdominal subcutaneous fat can be expressed as follows:

Area of abdominal subcutaneous fat≠(thickness of abdominal subcutaneous fat×waist size)

Figure 15:
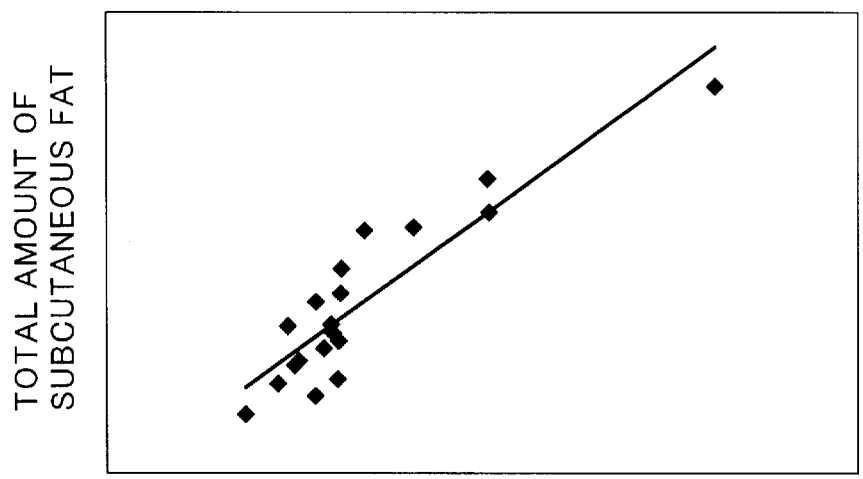
FIG. 15 is a view representing the correlation between a height, weight and thickness of subcutaneous fat, and a total amount of subcutaneous fat.

FIG. 15 shows the correlation between the estimated area and the actually measured area of said abdominal subcutaneous fat (the horizontal axis in the graph represents the estimated value which equals the product of waist size and thickness of abdominal subcutaneous fat). As the result, due to the fact that the actual human body is not a true circle in cross sectional shape, there may be some difference between the actual measured values and the estimated values. However, the regression curve appears substantially linear, and therefore, it is possible to estimate the area or amount of abdominal subcutaneous fat simply by measuring the waist size and the thickness of subcutaneous fat. FIG. 10 shows the correlation between the actually measured values of thickness and area of abdominal subcutaneous fat, that is effective to make the measuring process more easy. As the result, due to the correlation present therebetween, the regression curve can be used for estimating the area or amount of abdominal subcutaneous fat from the thickness of abdominal subcutaneous fat.

A. (3) Calculation of an area of abdominal visceral fat/an area of abdominal subcutaneous fat:

The area or amount of abdominal visceral fat is calculated by subtracting the area or amount of abdominal subcutaneous fat from the total area or mount of fat in abdomen. Then, the area or amount of abdominal visceral fat/the area or amount of abdominal subcutaneous fat is calculated.

Figure 11:
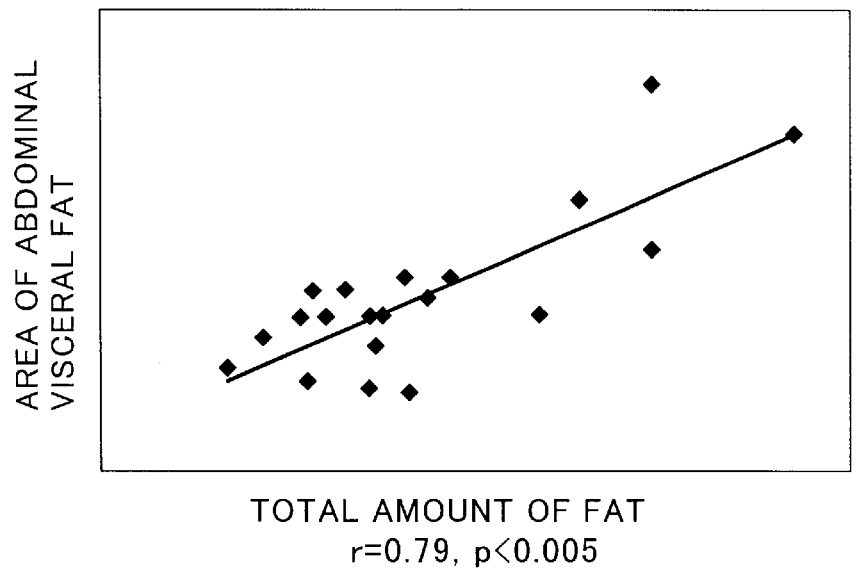
FIG. 11 is a view representing the correlation between a total amount of fat and an area of abdominal visceral fat.

B. (1) Calculation of an area of abdominal visceral fat:

The area or amount of abdominal visceral fat is calculated in relation to the total amount of fat (see FIG. 11).

B. (2) Calculation of an area of abdominal subcutaneous fat:

The area or amount of abdominal subcutaneous fat is calculated in relation to the thickness of subcutaneous fat, or the product of thickness of abdominal subcutaneous fat and waist size (see FIG. 10 or 16). Refer to description for item A. (2) above.

Figure 12:
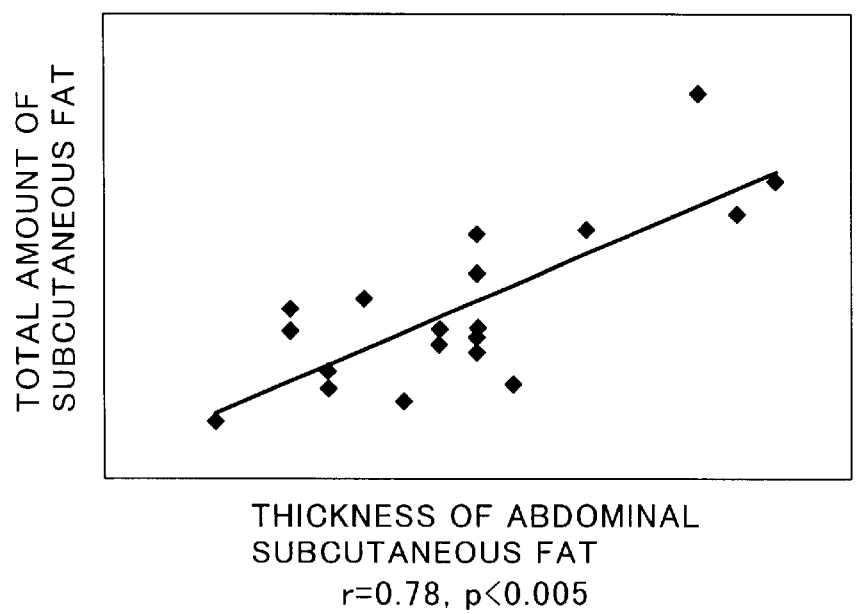
FIG. 12 is a view representing the correlation between a thickness of abdominal subcutaneous fat and a total amount of subcutaneous fat.

B. (3) Calculation of an area of abdominal visceral fat/an area of abdominal subcutaneous fat:

C. (1) Calculation of total amount of subcutaneous fat:

The total amount of subcutaneous fat is calculated in relation to the thickness of subcutaneous fat, or the product of thickness of subcutaneous fat and waist size (see FIG. 12 or 15).

A several formulas for deriving the body surface area have been published, one of which is described below:

$$\text{Total body surface area (cm}^2\text{)=weight (kg)}^{0.425} \times \text{height(cm)}^{0.725} \times 70.98$$

The rate of body surface area of a main body and limbs relative to the total body surface area is generally considered as about 80%. Then the following formula is resulted $$\text{Body surface area of a main body and limbs (cm}^2\text{)=total body surface area (cm}^2\text{)} \times 0.8$$

The thickness of subcutaneous fat in several parts of the body (for instance, thigh, crural, abdomen, flank, upper arm, etc.) is measured and the average of them is determined. Due to the fact that density of fat is 0.9 g/cm$^2$, the total amount of subcutaneous fat is calculated according to the following formula:

$$\text{Total amount of subcutaneous fat (g)=(body surface area of main body and limbs)} \times \text{(average thickness of subcutaneous fat)} \times 0.9$$

This is the most theoretical formula, but for the sake of simplicity, the total amount of subcutaneous fat may be calculated simply by using the values of thickness of subcutaneous fat in less number of parts of the body.

The part of the body having the largest amount of subcutaneous fat is abdomen, and therefore, it must have the greatest contribution to the total amount of subcutaneous fat. Accordingly the average thickness of subcutaneous fat is substituted by the thickness of subcutaneous fat in abdomen to produce an estimate of the total amount of subcutaneous fat. FIG. 15 shows the correlation between such estimated values of total amount of subcutaneous fat and the actually measured values therefor.

As the result, it is apparent that the values are substantially present on a line. Therefore, it is possible to estimate the total amount of subcutaneous fat from the thickness of subcutaneous fat in abdomen.

Alternatively, more facilitated method of getting the total amount of subcutaneous fat is to obtain the correlation between the thickness of subcutaneous fat in abdomen and the total amount of subcutaneous fat. Then, the regression curve is used to estimate the total amount of subcutaneous fat from the thickness of subcutaneous fat. FIG. 12 shows the relation between the thickness of subcutaneous fat in abdomen and the total amount of subcutaneous fat. Due to the correlation present therebetween, it is possible to use the regression curve for estimating the total amount of subcutaneous fat from the thickness of subcutaneous fat.

C. (2) Calculation of an amount of visceral fat:

The amount of visceral fat is calculated by subtracting the amount of subcutaneous fat from the total amount of fat.

Figure 13:
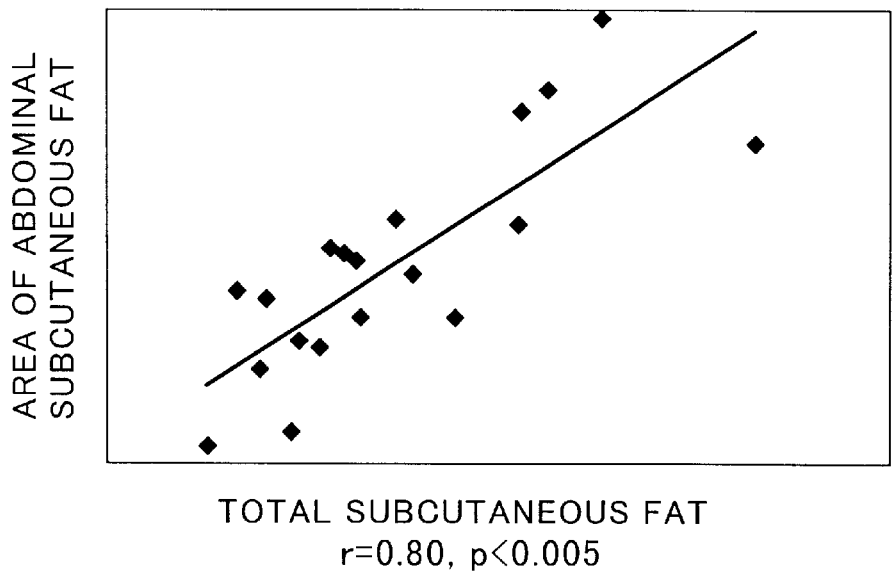
FIG. 13 is a view representing the correlation between a total subcutaneous fat and an area of abdominal subcutaneous fat.

C. (3) Calculation of an area of abdominal subcutaneous fat:

The area of abdominal subcutaneous fat is calculated in relation to the thickness of abdominal subcutaneous fat, or the product of thickness of subcutaneous fat and waist size (see FIG. 10 or 13). Refer to item A. (2) as above.

Figure 14:
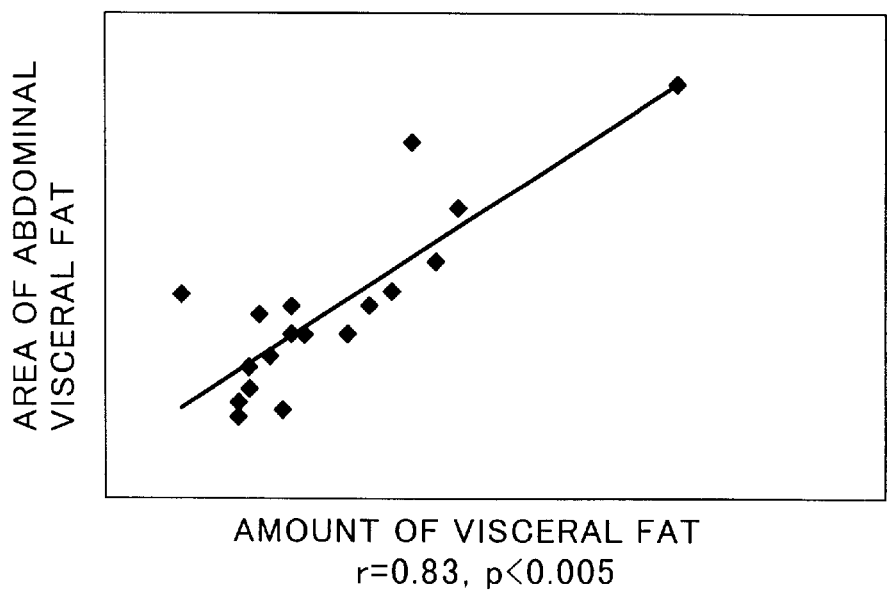
FIG. 14 is a view representing the correlation between an amount of visceral fat and an area of abdominal visceral fat.

C. (4) Calculation of an area of abdominal visceral fat:

The area of abdominal visceral fat is calculated in relation to the amount of area of visceral fat (see FIG. 14).

C. (5) Calculation of an area of abdominal visceral fat/area of abdominal subcutaneous fat:

Now, description is made to the criteria of evaluation for visceral fat. At the present time, an attack of diabetes or other "adult (noncommunicable) diseases" is considered more greatly depending on the visceral fat type corpulence than the subcutaneous fat type corpulence. Therefore, the tomographic image of the navel region obtained by CT scan or MRI is used to produce the values of the subcutaneous fat area and visceral fat area. Then, the boundary between both types of corpulence is set in such manner that the value of visceral fat area/subcutaneous fat area not less than 0.4 means the visceral fat type corpulence, while the value less than 0.4 means the subcutaneous fat type corpulence.

Figure 17:
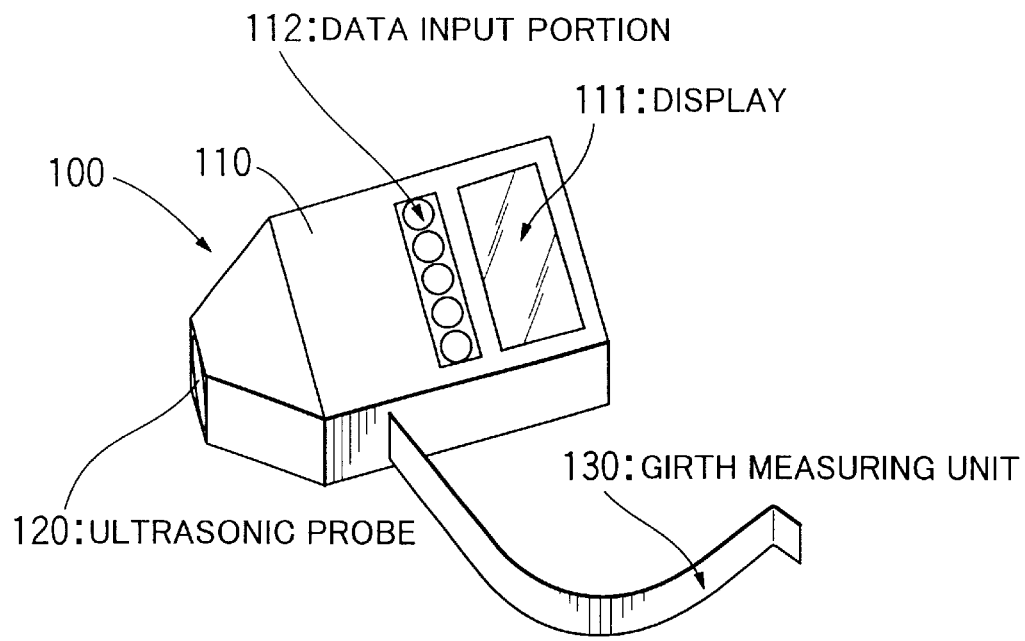
FIG. 17 is a perspective view representing an apparatus for measuring a body fat for a person according to yet further embodiment of the present invention.

FIG. 17 is a perspective view representing an apparatus for measuring a body fat for a person according to further embodiment of the present invention. The body fat measuring apparatus 100 includes a main housing 110, an ultrasonic probe 120 contained in the housing 110, and a girth measuring unit 130 such as a tape measure that is winded up and pulled out of the housing 110. A display 111 and a data input unit 112 are positioned on the top of the housing 110. A power switch (not shown) is positioned somewhere on the housing 110 and a control circuit including an arithmetic part is contained in the housing 110.

Figure 18:
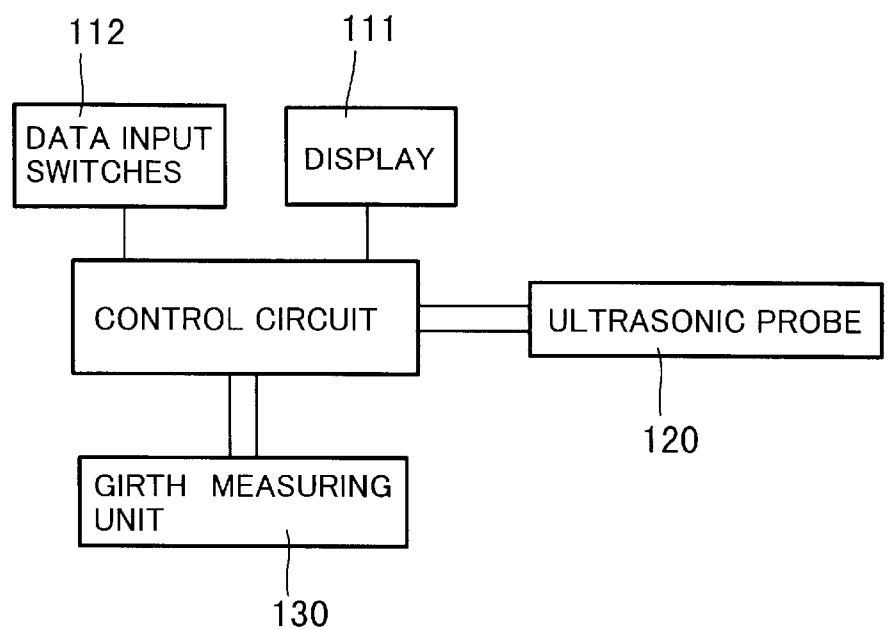
FIG. 18 is a schematic block diagram representing the circuit configuration of the body fat measuring apparatus, as shown in FIG. 17.

FIG. 18 is a schematic block diagram representing the circuit configuration of the body fat measuring apparatus 1 as shown in FIG. 17. As shown in FIG. 18, the body fat measuring apparatus 100 includes a control circuit as the main component in the housing 110. The control circuit functions to receive a data from input switches on the data input portion 112, a measurement data from the ultrasonic probe 120 and a measurement data from the girth measuring unit 130. Based on those data, the control circuit performs arithmetic operations, as described below, for indicating the results of the arithmetic operations on the display 111.

Figure 19:
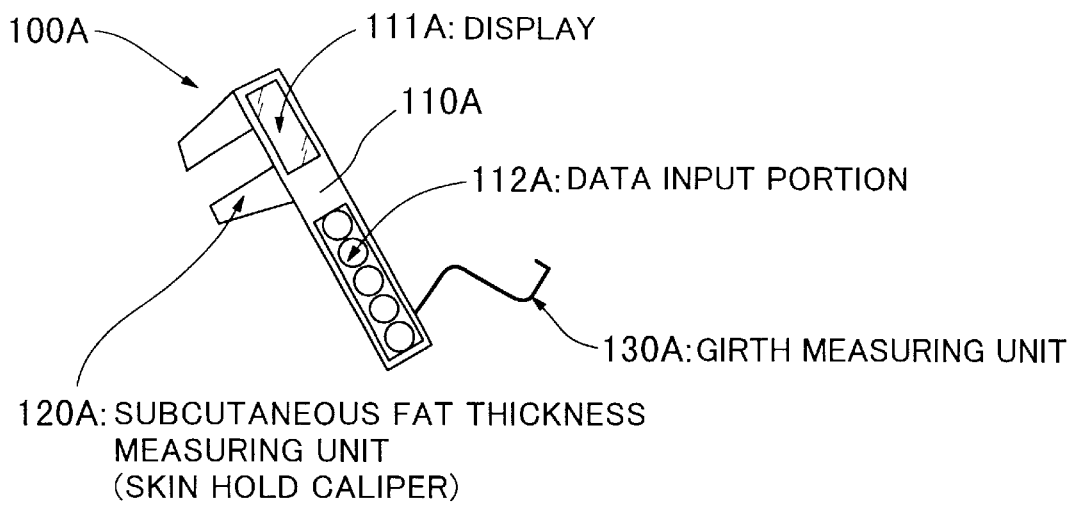
FIG. 19 is a perspective view representing an apparatus for measuring a body fat for a person according to yet further embodiment of the present invention.

FIG. 19 is a perspective view representing an apparatus for measuring a body fat for a person according to yet further embodiment of the present invention. The body fat measuring apparatus 100A includes a main housing 110A. A subcutaneous fat thickness measuring unit 120A such as a skin hold caliper is contained in the housing 110. The apparatus 100A includes a girth measuring unit 130A such as a tape measure that is winded up and pulled out of the housing 110. A display 111A and a data input unit 112A are positioned on the top of the housing 110A. A power switch (not shown) is positioned somewhere on the housing 110A and a control circuit including an arithmetic part is contained in the housing 110A.

Figure 20:
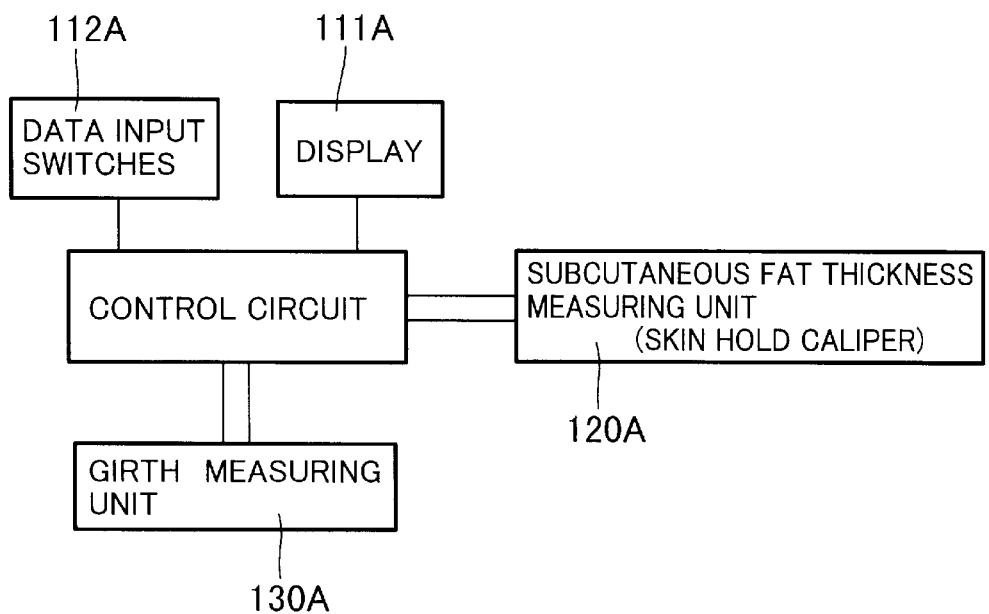
FIG. 20 is a schematic block diagram representing the circuit configuration of the body fat measuring apparatus, as shown in FIG. 19.

FIG. 20 is a schematic block diagram representing the circuit configuration of the body fat measuring apparatus, as shown in FIG. 19. As shown in FIG. 20, the body fat measuring apparatus 100A includes a control circuit as the main component in the housing 110A. The control circuit functions to receive a data from input switches on the data input portion 112A, a measurement data from the subcutaneous fat thickness measuring unit 120A and a measurement data from the girth measuring unit 130A. Based on those data, the control circuit performs arithmetic operations, as described below, for indicating the results of the arithmetic operations on the display 111A.

Now, a method for measuring a distribution of body fat for a person according to the present invention will be described, in association with the operation of the body fat measuring apparatus in the embodiments as described above.

Figure 21:
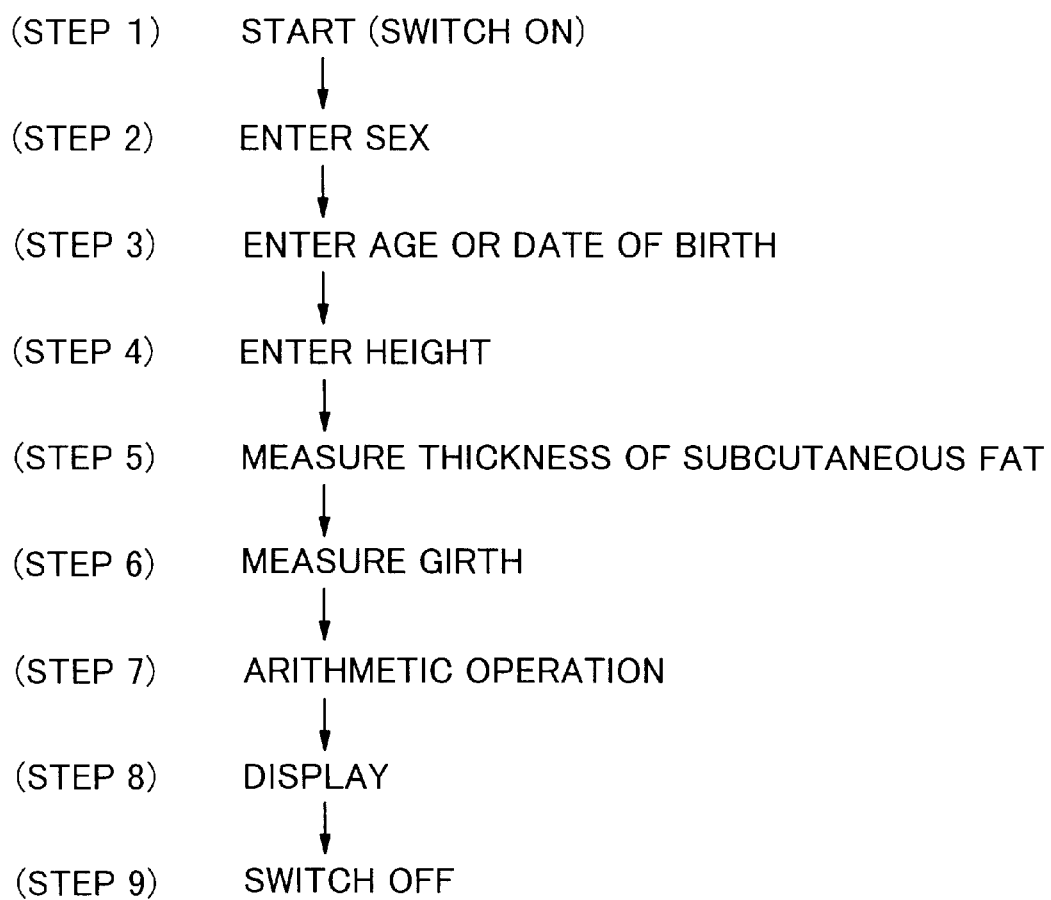
FIG. 21 is a flow chart briefly representing the steps of measuring the distribution of body fat according to the present invention.
Figure 22:
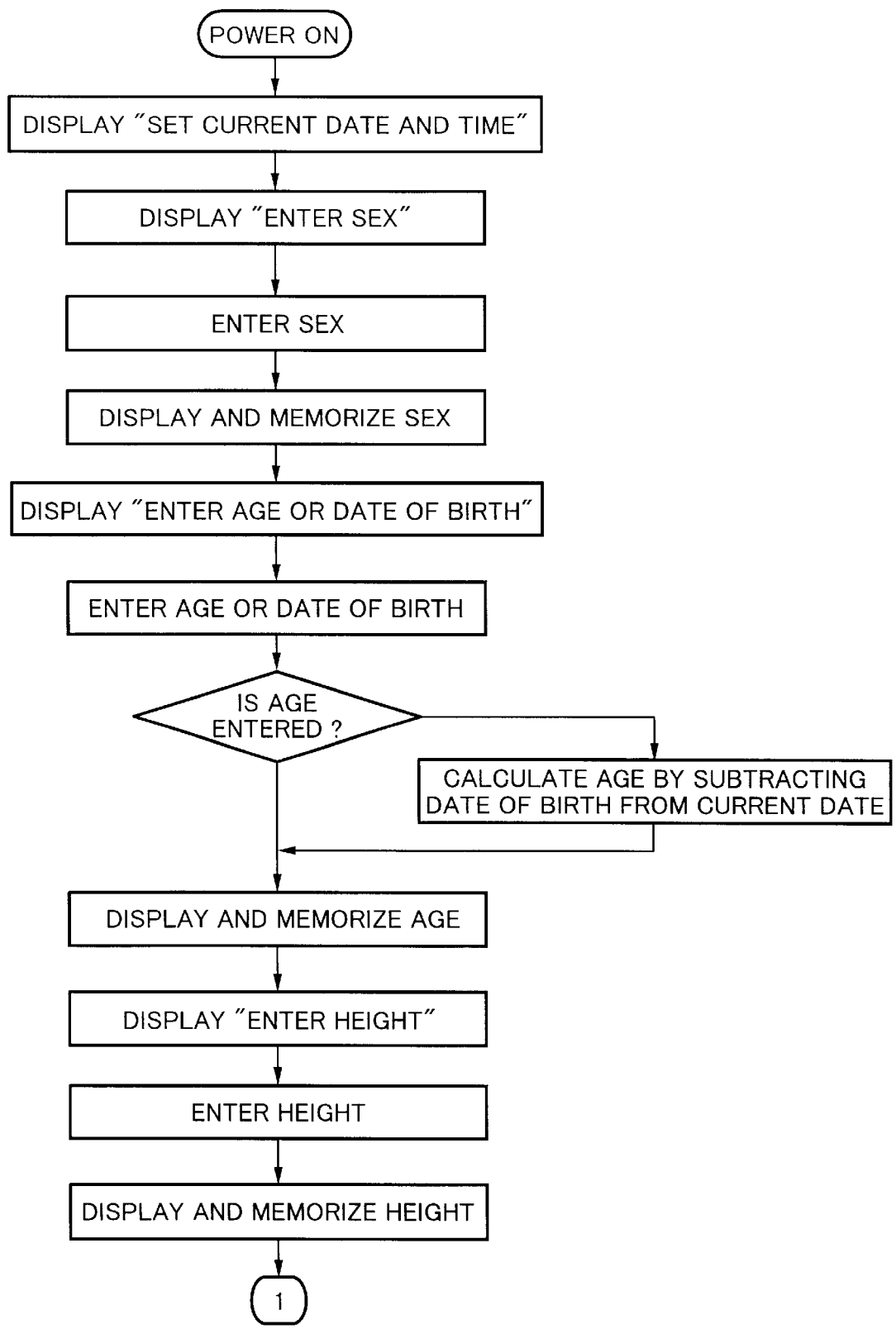
FIGS. 22 and 23 are flow charts representing in more detail the steps as shown in FIG. 21.
Figure 23:
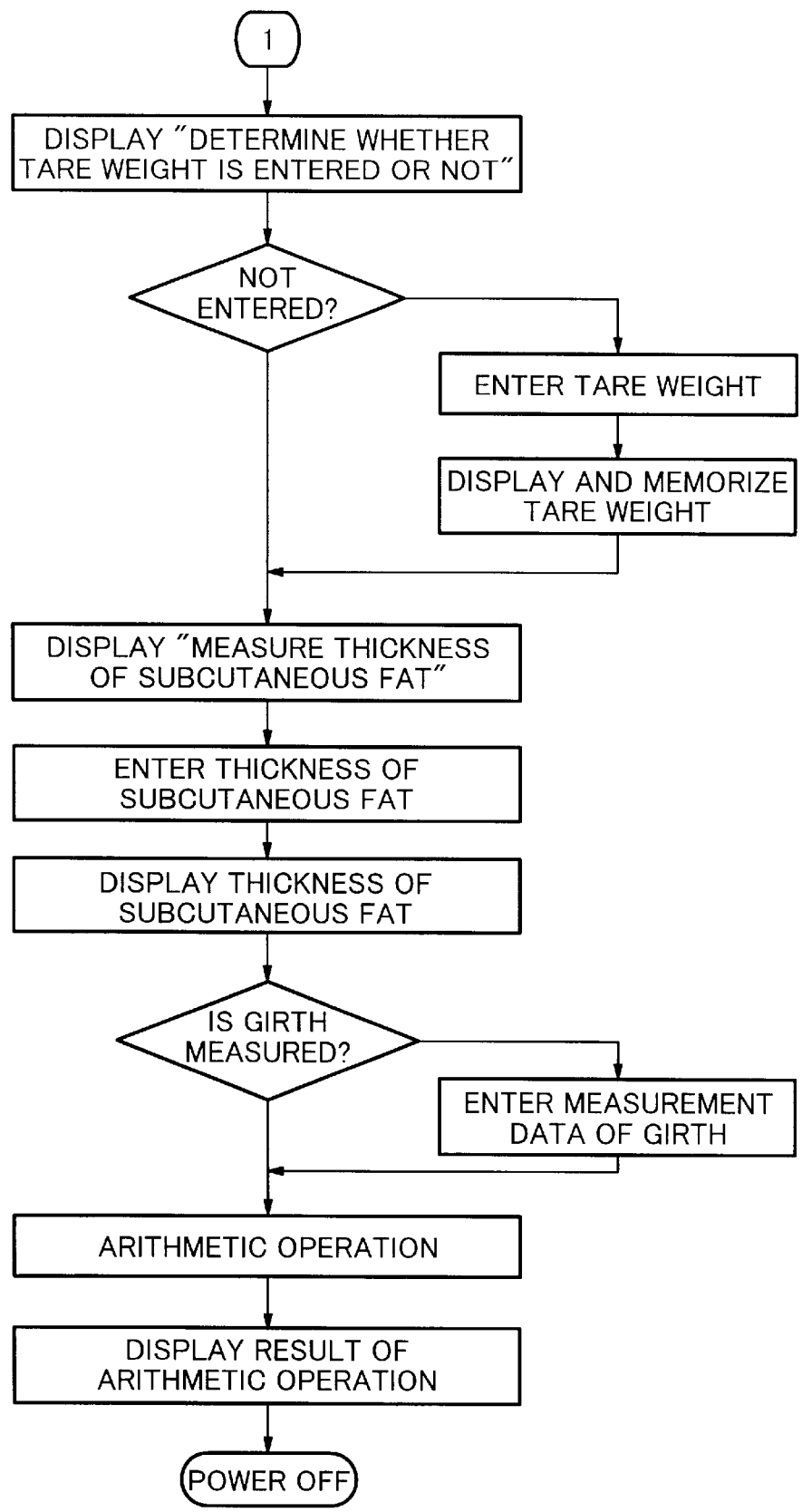

FIG. 21 is a flow chart briefly representing the steps of measuring the distribution of body fat according to the present invention. FIGS. 22 and 23 represent in more detail the steps as shown in FIG. 21 in the form of a flow chart. Referring to FIGS. 21 to 23, a person who wants to measure his distribution of body fat turns on the body fat measuring apparatus 100 or 100A, as shown in step 1 in FIG. 21. Then, in steps 2 to 4, he enters the personal data such as his height, age, sex, etc., into the apparatus 100 or 100A via the data input switches on the data input portion 112 or 112A.

Then, in step 5, the person measures the thickness of subcutaneous fat in his abdomen by using the ultrasonic probe 120 or the skin hold caliper 120A. In this connection, the measurement of the thickness of subcutaneous fat in abdomen by the ultrasonic probe 120 is performed in "A-mode" of operation. The measurement data on the thickness of subcutaneous fat in abdomen obtained by the ultrasonic probe 120 or the skin hold caliper 120A is transmitted to the control circuit within the housing 110 or 110A. Alternatively the person may read the measured value by the skin hold caliper 120A and then enter it into the apparatus 110A via the data input switches on the data input portion 112A.

Next, in step 6, the girth of a waist part of the person is measured by using the girth measuring unit 130 or 130A. Such data may automatically transmitted to the control circuit or it may read by the person, who then enter it into the control circuit using the data input switches.

Figure 24:
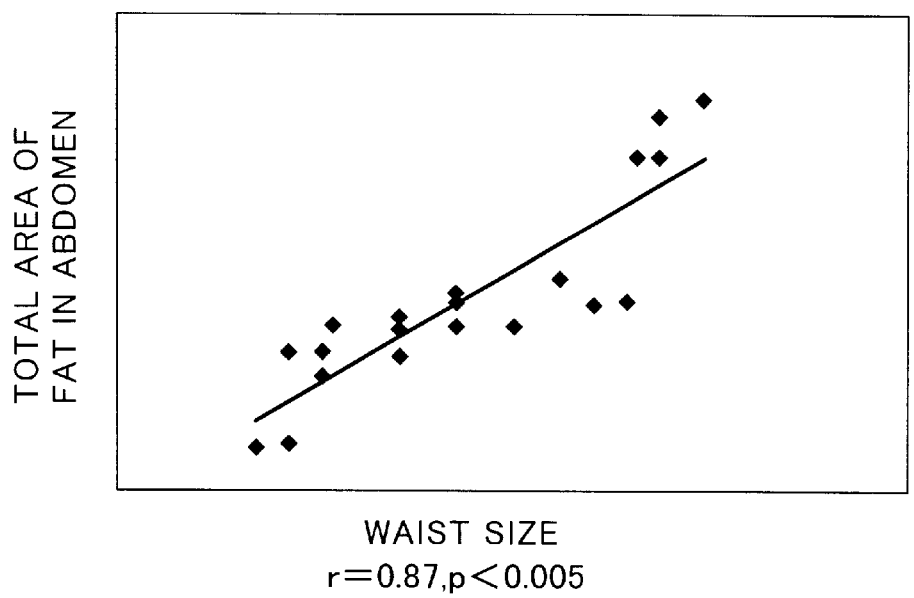
FIG. 24 is a view representing a correlation between a waist size and a total area of fat in abdomen.
Figure 25:
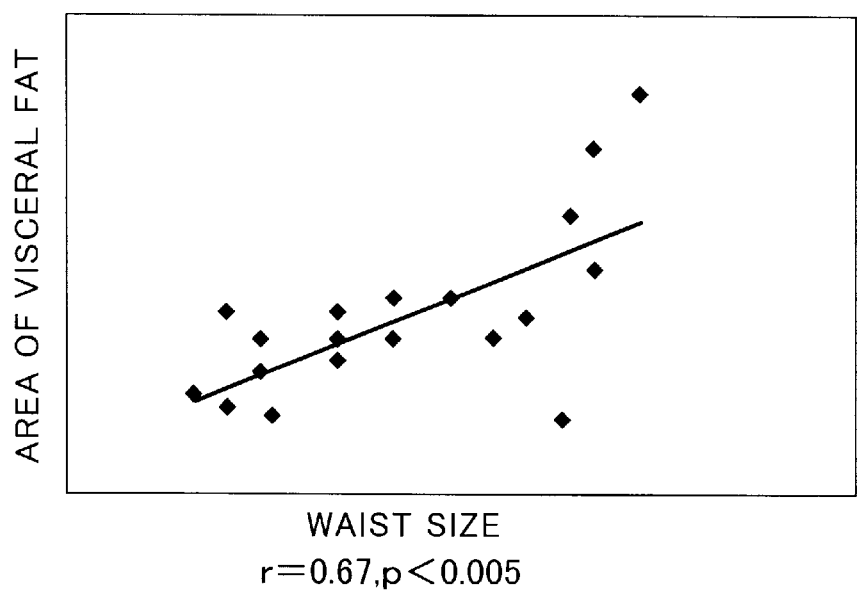
FIG. 25 is a view representing a correlation between a waist size and an area of visceral fat.

Based upon the data entered as described above, the arithmetic circuit within the control circuit performs a several operations as follows:

A. (1) Calculation of total area (or cross sectional area) of fat in abdomen:

The total area of fat in abdomen is calculated in relation to the waist size (see FIG. 24).

FIG. 24 represents one example of a regression curve for a man, 25 years old. It has found that such regression curve may vary to some degree depending upon the personal data such as sex, age, height, etc. Therefore, some correction process based upon such personal data is required for producing more precise estimation of the fat area.

A. (2) Calculation of an area (or cross sectional area) of subcutaneous fat in abdomen:

As described above, the area of subcutaneous fat in abdomen is calculated in relation to the thickness of abdominal subcutaneous fat, or the product of thickness of abdominal subcutaneous fat and waist size (see FIG. 10).

A. (3) Calculation of an area of abdominal visceral fat:

As described above, the area of abdominal visceral fat is calculated by subtracting the area of abdominal subcutaneous fat from the total area of fat in abdomen.

A. (4) Calculation of an area of abdominal visceral fat/an area of abdominal subcutaneous fat:

B. (1) Calculation of an area of abdominal visceral fat:

The area of abdominal visceral fat is calculated in relation to the waist size (see FIG. 9).

B. (2) Calculation of an area of abdominal subcutaneous fat:

As described above, the area of abdominal subcutaneous fat is calculated in relation to the thickness of subcutaneous fat, or the product of thickness of abdominal subcutaneous fat and waist size (see FIG. 10).

B. (3) Calculation of an area of abdominal visceral fat/an area of abdominal subcutaneous fat:

It is apparent from the foregoing that the present invention provides a new and improved method and apparatus for producing a several information useful for health care of a person with great simplicity and lower cost and without any adverse effect to the human body. The information thus produced includes, not only data of a body fat, but also data regarding a distribution of fat, such as an area or amount of visceral fat, an area or amount of subcutaneous fat, an area of abdominal visceral fat, and an area of abdominal subcutaneous fat.

In addition, the apparatus of the present invention, as described with reference to FIGS. 17 and 19, is designed to operate without having to measure the weight and the bioelectrical impedance. Therefore, it can easily be used even by a person with a pacemaker implanted and a pregnant woman with great safety.

What is claimed is:

1. A method of measuring a distribution of body fat for human body, characterized in that it comprises the steps of:
   measuring a bioelectrical impedance and a thickness of abdominal subcutaneous fat, based on personal data including at least one of sex, age, height, or weight; and
   calculating an area of abdominal visceral fat, based on the measurements of the bioelectrical impedance and the thickness of abdominal subcutaneous fat.

2. A method of measuring a distribution of body fat for human body, characterized in that it comprises the steps of:
   measuring a bioelectrical impedance and a thickness of abdominal subcutaneous fat, based on personal data including at least one of sex, age, height, or weight; and
   calculating an amount of abdominal visceral fat, based on the measurements of the bioelectrical impedance and the thickness of abdominal subcutaneous fat.

3. A method of measuring a distribution of body fat for human body, characterized in that it comprises the steps of:
   measuring a bioelectrical impedance and a thickness of abdominal subcutaneous fat, based on personal data including at least one of sex, age, height, or weight; and
   calculating an area of abdominal subcutaneous fat, based on the measurements of the bioelectrical impedance and the thickness of abdominal subcutaneous fat.

4. A method of measuring a distribution of body fat for human body, characterized in that it comprises the steps of:
   measuring a bioelectrical impedance and a thickness of abdominal subcutaneous fat, based on personal data including at least one of sex, age, height, or weight; and
   calculating an amount of abdominal subcutaneous fat, based on measurements of the bioelectrical impedance and the thickness of abdominal subcutaneous fat.

5. A method of measuring a distribution of body fat for human body, characterized in that it comprises the steps of:
measuring a bioelectrical impedance and a thickness of abdominal subcutaneous fat, based on personal data including at least one of sex, age, height, or weight; and
calculating an area of abdominal visceral fat and an area of abdominal subcutaneous fat, based on the measurements of the bioelectrical impedance and the thickness of abdominal subcutaneous fat.

6. A method of measuring a distribution of body fat for human body, characterized in that it comprises the steps of:
measuring a bioelectrical impedance and a thickness of abdominal subcutaneous fat, based on personal data including at least one of sex, age, height, or weight; and
calculating an amount of abdominal visceral fat and an amount of abdominal subcutaneous fat, based on the measurements of the bioelectrical impedance and the thickness of abdominal subcutaneous fat.

7. A method of measuring a distribution of body fat for human body, characterized in that it comprises the steps of:
measuring a bioelectrical impedance and a thickness of abdominal subcutaneous fat, based on the sex, age, height and weight of a person;
measuring a girth of abdomen; and
calculating an area of abdominal visceral fat, based on the measurements of the bioelectrical impedance, the thickness of abdominal subcutaneous fat and the girth of abdomen.

8. A method of measuring a distribution of body fat for human body, characterized in that it comprises the steps of:
measuring a bioelectrical impedance and a thickness of abdominal subcutaneous fat, based on the sex, age, height and weight of a person;
measuring a girth of abdomen; and
calculating an amount of abdominal visceral fat, based on the measurements of the bioelectrical impedance, the thickness of abdominal subcutaneous fat and the girth of abdomen.

9. A method according claim 1 in which said thickness of abdominal subcutaneous fat is measured by using an ultrasonic signal.

10. A method according claim 1 in which said thickness of abdominal subcutaneous fat is measured by using a skin hold caliper.

11. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat; and
an arithmetic element that calculates an area of abdominal visceral fat, based on the data from said first input unit, said measuring unit and said second input unit.

12. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat; and
an arithmetic element that calculates an amount of abdominal visceral fat, based on the data from said first input unit, said measuring unit and said second input unit.

13. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat; and
an arithmetic element that calculates an area of abdominal subcutaneous fat, based on the data from said first input unit, said measuring unit and said second input unit.

14. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat; and
an arithmetic element that calculates an amount of abdominal subcutaneous fat, based on the data from said first input unit, said measuring unit and said second input unit.

15. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat;
a third input unit that enters a girth of abdomen; and
an arithmetic element that calculates an area of abdominal visceral fat, based on the data from said first input unit, said measuring unit, said second input unit and said third input unit.

16. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat;
a third input unit that enters a girth of abdomen; and
an arithmetic element that calculates an amount of abdominal visceral fat, based on the data from said first input unit, said measuring unit, said second input unit and a third input unit.

17. An apparatus for measuring a distribution of body fat for human body, characterized in that it comprises:
a first input unit that enters personal data including at least one of sex, age, height, or weight;
a measuring unit that measures a bioelectrical impedance;
a second input unit that enters a thickness of abdominal subcutaneous fat;
a third input unit that enters a girth of abdomen; and
an arithmetic element that calculates an area of abdominal subcutaneous fat, based on the data from said first input unit, said measuring unit, said second input unit and said third input unit.

18. An apparatus for measuring a distribution of body fat for human body, characterized in that it comprises:
a first input unit that enters personal data including at least one of sex, age, height, or weight;
a measuring unit that measures a bioelectrical impedance;

a second input unit that enters a thickness of abdominal subcutaneous fat;

a third input unit that enters a girth of abdomen; and an arithmetic element that calculates an amount of abdominal subcutaneous fat, based on the data from said first input unit, said measuring unit, said second input unit and third input unit.

19. An apparatus for measuring a distribution of body fat for human body, characterized in that it comprises:

a first input unit that enters personal data including at least one of sex, age, height, or weight;

a measuring unit that measures a bioelectrical impedance;

a second input unit that enters a thickness of abdominal subcutaneous fat; and an arithmetic element that calculates an area of abdominal visceral fat and an area of abdominal subcutaneous fat, based on the data from said first input unit, said measuring unit and said second input unit.

20. An apparatus for measuring a distribution of body fat for human body, characterized in that it comprises:

a first input unit that enters personal data including at least one of sex, age, height, or weight;

a measuring unit that measures a bioelectrical impedance;

a second input unit that enters a thickness of abdominal subcutaneous fat; and an arithmetic element that calculates an amount of abdominal visceral fat and an amount of abdominal subcutaneous fat, based on the data from said first input unit, said measuring unit and said second input unit.

21. An apparatus according claim 11 in which said second input unit includes an ultrasonic probe.

22. An apparatus according to claim 21 in which the data detected by said ultrasonic probe is transmitted to said arithmetic element via a radio communication means or an optical communication means.

23. An apparatus according claim 11 in which said second input unit includes a skin hold caliper.

24. An apparatus according to claim 23 in which the data detected by said skin hold caliper is transmitted to said arithmetic element via a radio communication means or an optical communication means.

25. An apparatus for measuring a distribution of body fat for human body, characterized in that it comprises:

a first arithmetic element that calculates an area of abdominal visceral fat;

a second arithmetic element that calculates an area of abdominal subcutaneous fat; and a decision unit that determines the type of corpulence by dividing the area of abdominal visceral fat calculated in said first arithmetic element by the area of abdominal subcutaneous fat calculated in said second arithmetic element.

26. A method of measuring a distribution of body fat for human body, characterized in that it comprises the steps of:

measuring a thickness of abdominal subcutaneous fat and a girth of abdomen; and calculating an area of abdominal visceral fat, based upon the measurements of the thickness of abdominal subcutaneous fat and the girth of abdomen.

27. A method of measuring a distribution of body fat for human body, characterized in that it comprises the steps of:

measuring a thickness of abdominal subcutaneous fat and a girth of abdomen; and calculating an area of abdominal subcutaneous fat, based upon the measurements of the thickness of abdominal subcutaneous fat and the girth of abdomen.

28. A method of measuring a distribution of body fat for human body, characterized in that it comprises the steps of:

measuring a thickness of abdominal subcutaneous fat and a girth of abdomen; and calculating an area of abdominal visceral fat and an area of abdominal subcutaneous fat, based upon the measurements of the thickness of abdominal subcutaneous fat and the girth of abdomen.

29. A method according to claim 26, in which said thickness of abdominal subcutaneous fat is measured by using an ultrasonic signal.

30. A method according to claim 26, in which said thickness of abdominal subcutaneous fat is measured by using a skin hold caliper.

31. A method according to any one of claims 26 to 30 in which the step of deriving the area of abdominal visceral fat or the area of abdominal subcutaneous fat further comprises the step of performing a correction process based upon personal data including at least one of sex, age, or height.

32. An apparatus for measuring a distribution of body fat for human body, characterized in that it comprises:

a first input unit that enters a thickness of abdominal subcutaneous fat;

a second input unit that enters a girth of abdomen; and an arithmetic element that calculates an area of abdominal visceral fat based upon the data from said first and second input units.

33. An apparatus according to claim 32 in which said first input unit includes an ultrasonic probe.

34. An apparatus according to claim 32 in which said first input unit includes a skin hold caliper.

35. An apparatus according to claim 32, 33 or 34 in which it further comprises a third input unit that enters personal data including at least one of sex, age, or height.

36. A method of measuring body fat for human body, characterized in that it comprises the steps of:

measuring a bioelectrical impedance between two parts of a person; and calculating an area or amount of abdominal visceral fat based on the measurements of said bioelectrical impedance between the two parts of the person and the age, the height, and the weight of the person.

37. A method of measuring body fat for human body, characterized in that it comprises the steps of:

measuring a bioelectrical impedance between two parts of a person;

calculating a total amount of fat based on the measurements of said bioelectrical impedance between the two parts of the person and the age, the height, and the weight of the person; and calculating an area or amount of abdominal visceral fat based on the calculated total amount of fat.

38. A method according to claim 36 or 37 in which said two parts are both feet.

39. A method according to claim 36 or 37 in which said two parts are both hands.

40. A method according to claim 36 or 37 in which said two parts are a hand and a foot.

41. An apparatus for measuring body fat for human body, characterized in that it comprises:

an input unit that enters at least one personal data including age, height, and weight;

a measuring unit that measures bioelectrical impedance between two parts of a person; and an arithmetic element that calculates an area or amount of abdominal visceral fat based on the data from said input unit and said measuring unit.

42. An apparatus for measuring body fat for human body, characterized in that it comprises:

an input unit that enters at least one personal data including age, height, and weight;

a measuring unit that measures a bioelectrical impedance between two parts of a person; and an arithmetic element that calculates a total amount of fat based on the data from said input unit and said measuring unit, and calculates an area or amount of abdominal visceral fat based on said total amount of fat.

43. An apparatus according to claim 41 or 42 in which said two parts are both feet.

44. An apparatus according to claim 41 or 42 in which said two parts are both hands.

45. An apparatus according to claim 41 or 42 in which said two parts are a hand and a foot.

46. A method of measuring body fat for human body, characterized in that it comprises the steps of:

inputting a girth of abdomen; and calculating a total area of fat in abdomen based on the inputted girth of abdomen and personal data including at least a height.

47. A method of measuring body fat for human body, characterized in that it comprises the steps of:

inputting girth of abdomen; and calculating an area of visceral fat based on the inputted girth of abdomen and personal data including at least height.

48. A method according to claim 46 or 47 in which the girth of abdomen is inputted by a girth measuring unit.

49. A method according to claim 46 or 47 in which the girth of abdomen is inputted by data input switches.

50. An apparatus for measuring body fat for human body, characterized in that it comprises:

a first input unit that enters a girth of abdomen;

a second input unit that enters a personal data including at least a height; and an arithmetic element that calculates total area of fat in abdomen based on the data from said first input unit and second input unit.

51. An apparatus for measuring body fat for human body, characterized in that it comprises:

a first input unit that enters a girth of abdomen;

a second input unit that enters personal data including at least height; and an arithmetic element that calculates an area of visceral fat based on the data from said first input unit and second input unit.

52. An apparatus according to claim 50 or 51 in which said first input unit is a girth measuring unit.

53. An apparatus according to claim 50 or 51 in which said first input unit is data input switches.

54. An apparatus according to claim 50 or 51 in which said second input unit is data input switches.

55. An apparatus according to claim 50 or 51, further comprising a third input unit that enters the personal data including at least one of sex and age.

* * * * *